(12) United States Patent
Bissinger et al.

(10) Patent No.: US 7,662,869 B2
(45) Date of Patent: Feb. 16, 2010

(54) DENTAL COMPOSITION CONTAINING UNSATURATED CARBOSILANE CONTAINING COMPONENTS

(75) Inventors: Peter Bissinger, Diessen (DE); Adrian S. Eckert, Munich (DE); Reinhold Hecht, Kaufering (DE); Uwe H. Hoheisel, Turkenfeld (DE)

(73) Assignee: 3M Innovative Properties Company, St. Paul, MN (US)

( * ) Notice: Subject to any disclaimer, the term of this patent is extended or adjusted under 35 U.S.C. 154(b) by 302 days.

(21) Appl. No.: 11/572,071

(22) PCT Filed: Jul. 14, 2004

(86) PCT No.: PCT/EP2004/007788

§ 371 (c)(1),
(2), (4) Date: Jan. 12, 2007

(87) PCT Pub. No.: WO2006/005368

PCT Pub. Date: Jan. 19, 2006

(65) Prior Publication Data

US 2008/0070193 A1 Mar. 20, 2008

(51) Int. Cl.
*C08G 77/12* (2006.01)
*C08G 77/20* (2006.01)
*C08G 77/00* (2006.01)
*C07F 7/08* (2006.01)
*A61C 5/08* (2006.01)
*A61C 5/00* (2006.01)
*A61K 6/093* (2006.01)
*C08F 30/08* (2006.01)
*A61K 6/02* (2006.01)
*A61K 6/08* (2006.01)

(52) U.S. Cl. ............... 523/116; 523/115; 523/118; 528/31; 528/32; 528/33; 556/432; 433/222.1; 433/228.1; 433/226; 106/35; 526/279

(58) Field of Classification Search ............... 523/116, 523/118, 115; 433/217.1, 222.1, 228.1, 226; 106/35; 526/279; 528/31, 32, 33, 43; 556/432
See application file for complete search history.

(56) References Cited

U.S. PATENT DOCUMENTS

| | | | |
|---|---|---|---|
| 3,715,334 A | 2/1973 | Karstedt | |
| 3,775,352 A | 11/1973 | Leonard | |
| 3,814,730 A | 6/1974 | Karstedt | |
| 3,927,116 A | 12/1975 | Rick et al. | |
| 3,933,880 A | 1/1976 | Bergstrom et al. | |
| 3,971,754 A | 7/1976 | Jurecic | |
| 4,391,590 A | 7/1983 | Dougherty | |
| 4,704,438 A * | 11/1987 | Niwa et al. ............... 525/333.3 |
| 4,767,798 A | 8/1988 | Gasser et al. | |
| 4,788,268 A | 11/1988 | Lau et al. | |
| 5,145,886 A | 9/1992 | Oxman et al. | |
| 5,165,890 A | 11/1992 | Discko | |
| 5,233,006 A | 8/1993 | Wolter et al. | |
| 5,322,440 A | 6/1994 | Steele | |
| 5,367,001 A * | 11/1994 | Itoh et al. ............... 523/109 |
| 5,691,433 A * | 11/1997 | Kotani et al. ............... 528/15 |
| 6,046,250 A | 4/2000 | Boardman et al. | |
| 6,245,828 B1 | 6/2001 | Weinmann et al. | |
| 6,335,413 B1 | 1/2002 | Zech et al. | |
| 6,376,569 B1 | 4/2002 | Oxman et al. | |
| 6,566,413 B1 | 5/2003 | Weinmann et al. | |
| 6,624,236 B1 | 9/2003 | Bissinger et al. | |
| 6,653,375 B2 | 11/2003 | Moszner et al. | |
| 6,852,822 B1 * | 2/2005 | Bissigner et al. ............... 528/32 |
| 2002/0082315 A1 | 6/2002 | Moszner et al. | |
| 2003/0035899 A1 | 2/2003 | Klettke et al. | |
| 2003/0166816 A1 | 9/2003 | Bissinger et al. | |
| 2004/0110863 A1 | 6/2004 | Zech et al. | |

FOREIGN PATENT DOCUMENTS

| | | |
|---|---|---|
| EP | 0 238 025 A2 | 9/1987 |
| EP | 0 451 709 A2 | 10/1991 |
| EP | 1 368 402 A1 | 12/2003 |
| EP | 1 512 724 A1 | 9/2005 |
| WO | WO 00/38619 | 7/2000 |
| WO | WO 01/07444 A1 | 2/2001 |
| WO | WO 01/92271 A1 | 12/2001 |
| WO | WO 01/95862 A1 | 12/2001 |
| WO | WO 02/066535 A1 | 8/2002 |
| WO | WO 2006/005363 A1 | 1/2006 |
| WO | WO 2006/005366 A1 | 1/2006 |
| WO | WO 2006/005368 A1 | 1/2006 |

OTHER PUBLICATIONS

Beck, H., N., Chaffee, R., G., Phenenyl Silicon Compounds, J. Chem. Eng. Data 1963, 8(3), 453-454.
Houben-Weyl, Methoden d. Organ. Chemie, vol. VI/3, p57 (1st preparation example) or p56 (1st prep. example), Georg Thieme Verlag, Stuttgart, 1965, 4. edition.
Houben-Weyl, Methoden d. Organ. Chemie, vol. XIII/2a, p47ff., Georg Thieme Verlag, Stuttgart, 1973, 4. edition.

(Continued)

*Primary Examiner*—Mark Eashoo
*Assistant Examiner*—Michael Pepitone
(74) *Attorney, Agent, or Firm*—Pamela L. Stewart

(57) ABSTRACT

The invention relates to a dental composition comprising a) carbosilane containing component (A) comprising at least 1 Si-Aryl bond, at least 1 silicon atom, at least 2 unsaturated moiety, no Si—Oxygen bond, b) Si—H functional component (B), c) initiator (C), d) optionally filler (D), and e) optionally component (E) selected from modifiers, dyes, pigments, thixotropic agents, flow improvers, polymeric thickeners, surfactants, odorous substances, diluting agent(s) and flavorings.

37 Claims, No Drawings

OTHER PUBLICATIONS

Marciniec, B., Comprehensive Handbook on Hydosilylation, Pergamon press, Oxford, 1992.

Marciniec, B., Comprehensive Handbook on Hydrosilylation, p8ff, Pergamon Press, Oxford, 1992.

Marciniec, B., Comprehensive Handbook on Hydrosilylation, p107ff., Pergamon Press, Oxford, 1992.

Tarbell, D., S., Wilson, J., W., The Rearrangement of 4-Crotyloxy-3,5-Dichlorobenzoic Acid, J.Am.Chem.Soc. 1942, 64(5), 1066-1070.

DIN EN ISO 4049, Jan. 2001.

DIN EN ISO 9917-1, Apr. 2004.

DIN EN ISO 9917-2, Oct. 1999.

* cited by examiner

DENTAL COMPOSITION CONTAINING UNSATURATED CARBOSILANE CONTAINING COMPONENTS

CROSS REFERENCE TO RELATED APPLICATIONS

This application is a national stage filing under 35 U.S.C. 371 of PCT/EP2004/007788, filed Jul 14, 2004.

The invention relates to a curable dental composition containing an unsaturated carbosilane component. The composition has improved properties and can be used e.g. as a dental filling material.

The dental filling materials on the market can generally be divided into composites, resin modified glass ionomer cements and glass ionomer cements (GIZ). The composites cure usually via a light induced radical polymerisation of unsaturated components, especially (meth)acrylates. The glass ionomer cements cure by a cement setting reaction, whereas in resin modified glass ionomer cements curing is achieved using both mechanisms.

Of special interest are the dental composites, the curing of which results in a very hard material compared to glass ionomer cements which is especially useful for filling teeth cavities. However, a well known disadvantage of the dental composites on the market is that the compositions shrink on curing. A further drawback is, that some of the components of the dental composite materials are not hydrolytically very stable and/or comparable hydrophilic and thus harmful substances can emerge from the cured composition over the years.

Attempts were made to solve the above mentioned problems.

In this respect U.S. Pat. No. 6,653,375 B2 describes urethane di(meth)acrylate derivatives of 1,3-bis(1-isocyanato-1-1methylethyl)benzene. It is stated that the monomers have a refractive index compatible with that of customary dental filling materials, do not tend towards discolorations and can replace bis-GMA in dental materials without impairing the mechanical properties of the materials.

U.S. Pat. No. 6,624,236 B1 is directed to cyclosiloxane-based crosslinkable monomers, production thereof and use thereof in polymerisable materials, in particular to polysiloxanes from sol-gel-condensable cyclosiloxane (meth)acrylates as well as resinous compositions.

U.S. Pat. No. 6,566,413 B1 relates to polymerisable materials based on hardenable siloxane compounds useful for dental compositions. It is described that the siloxane compounds used display a low viscosity, permit a high filler uptake and lead to compositions with a low polymerisation shrinkage.

In WO 01/92271 A1 prepolymeric (meth)acrylates with polycyclic or aromatic segments are described useful for the preparation of dental materials. It is said that the siloxane monomers have a high molecular weight (e.g. over 600 g/mol), have a high (meth)acrylate functionality and a low viscosity.

WO 2001095862 A1 refers to a low shrinking polymerisable dental material including a mixture of di- or poly(meth) acrylate, an alkoxylated bisphenol dimethacrylate, a polymerisable monomer, a polymerisation initiator and/or sensitizer, a stabilizer and a filler. It is mentioned that the volumetric shrinkage during polymerisation is less than 2 vol-%.

EP 0 451 709 A2 describes silanes of a certain formula which can comprise groups containing (meth)acrylate moieties. It is stated that the silanes can be used as such or as additives for coating compositions, bulk materials, adhesives and compositions for injection moulding.

The solutions described above, however, are not completely satisfying.

Therefore, there is a need for alternatives. There is especially a need for alternative materials with improved properties.

It is thus an object of the invention to alleviate one or more of the problems mentioned above.

It is also an object of the invention to provide an esthetical composition useful in the dental field.

It is another object of the invention to provide a lipophilic composition.

It is a further object of the invention to provide a composition with improved properties, especially a composition which enables one to provide a composition having a low shrinkage value.

It has been found that one or more of the above mentioned objects can be achieved by providing a composition as described in the text below.

Surprisingly, it has been found that using carbosilane compounds comprising polymerizable groups such as unsaturated groups and not containing carbosiloxane structures enables one to provide curable dental compositions with improved properties.

Thus, the invention relates to a dental composition comprising
a) carbosilane containing component (A) comprising
  at least 1 Si-Aryl bond,
  at least 1 silicon atom,
  at least 2 unsaturated moiety,
  no Si—Oxygen bond,
b) Si—H functional component (B),
c) initiator (C),
d) optionally filler (D),
e) optionally component (E) selected from modifiers, dyes, pigments, thixotropic agents, flow improvers, polymeric thickeners, surfactants, odorous substances, diluting agent(s) and flavourings.

The invention also relates to a method of producing the composition as described in the text below.

Additionally, the invention relates to a method of using the composition as described in the text below.

Carbosilane containing component (A) can be used alone or in a mixture with other unsaturated components as reactive compounds in dental materials that may also contain other reactive and/or unreactive compounds, if needed.

Carbosilane containing component (A) usually shows a comparably high refractive index together with a comparably low viscosity so that the dental compositions provided usually have a good opacity and thus are highly esthetic. Moreover, the compositions show comparably low shrinkage as well as low uptake of water and/or water soluble dyes (e.g. from coffee, tea, red wine) after curing compared to other dental compositions on the market.

The terms "comprise" and "contain" within the meaning of the invention introduce a non exhaustive list of features. Likewise, the word "one" or "a" is to be understood in the sense of "at least one".

The term "dental composition" according to the invention is a curable composition to be used in the dental field for different purposes, usually in small amounts of a few grams.

The term "Si—H functional component" according to the invention is a substance or mixture of substances each containing at least 1 Si atom and at least 1 H atom directly attached to a Si atom within the molecule.

The term "initiator" according to the invention is a substance or mixture of substances capable of starting a curing reaction, preferably a hydrosilylation curing reaction.

The term "unsaturated moiety" according to the invention refers to a moiety which is polymerizable, especially via hydrosilylation reaction, comprising preferably a terminal olefinic group.

The term "aryl" according to the invention refers to an aromatic moiety such as phenyl or naphthyl. Besides an attached Si-Atom, the aryl moiety can bear 1, 2 or 3, preferably 1 or 2 substituents, preferably alkyl and/or aryl ether groups (e.g. $C_{1-8}$ alkyl, $C_{2-10}$ alkenyl, $C_{3-6}$ cycloalkyl, $C_{4-6}$ cycloalkenyl, $C_{6-10}$ aryl) and/or an allyl group.

Carbosilane containing component (A) can be synthesized e.g. via hydrosilylation reaction (cf. Marciniec, B., Comprehensive Handbook on Hydrosilylation, Pergamon Press, Oxford, 1992) or e.g. via Grignard reaction (cf. Houben-Weyl, Methoden der Organischen Chemie, volume XIII/2a, p 47ff., Georg Thieme Verlag, Stuttgart, 1973, 4. edition).

The hydrosilylation reaction is an addition reaction where a Si—H functional compound (i) is added to an olefinic functional compound (ii) in the presence of a catalyst as indicated in scheme (I) forming a new Si—C single bond and yielding silicon containing compound (iii):

scheme (I)

wherein $R_1$, $R_2$, $R_3$, $R_4$=(cyclo)aliphatic or aromatic or (cyclo)aliphatic aromatic or aromatic (cyclo)aliphatic moiety, wherein C and/or H atoms can be substituted by e.g. O, Br, Cl, and Si atoms and can also contain other functionalities like olefinic groups.

That is, carbosilane containing component (A) of the invention can be obtained via hydrosilylation reaction according to scheme (I) by reacting poly Si—H functional carbosilane component (i) with diolefinic or acetylenic component (ii) using e.g. common noble metal compounds as catalyst as described e.g. in Marciniec, B., Comprehensive Handbook on Hydrosilylation, p 107ff., Pergamon Press, Oxford, 1992 or e.g. for similar siloxane based compounds in U.S. Pat. No. 6,245,828 (first step of syntheses of preparation examples 2-3 in column 19).

Poly Si—H functional carbosilane components (i) like 1,3,5-Tris(dimethylsilyl)benzene and 2,4,6-Tris(dimethylsilyl)anisole can be synthesized via in situ Grignard reaction as e.g. described by Beck, H., N., Chaffee, R., G., *J. Chem. Eng. Data* 1963, 8(3), 453-454.

Diolefinic or acetylenic components (ii) like Acetylene or 1,5-Hexadiene are commercially available.

Carbosilane containing component (A) of the invention can also be obtained via Grignard reaction according to scheme (II) by reacting (poly)organometallic functional component (iv) with silicon containing component (v).

The Grignard reaction is a nucleophilic substitution reaction where a metal organic compound (iv) is substituting a leaving group LG of e.g. a silicon containing compound (v) as indicated in scheme (II) forming a new Si—C single bond and yielding a silicon containing compound (vi) forming a new Si—C single bond and yielding silicon containing compound (vi):

scheme (II)

wherein $R_5$, $R_6$, $R_7$, $R_8$=(cyclo)aliphatic or aromatic or (cyclo)aliphatic aromatic or aromatic (cyclo)aliphatic moiety, wherein C and/or H atoms can also be substituted by e.g. O, Br, Cl, and Si atoms and can also contain olefinic groups.

Metal organic compound (iv) can be used according to scheme (II) as described e.g. for similar siloxane based compounds in U.S. Pat. No. 4,788,268 (preparation examples 1, 2, 4, 5, 6, and 7 in columns 6-17) as an intermediate of an in situ Grignard reaction starting from halogenated precursors via an in situ Grignard reaction as e.g. described for other carbosilane compounds like 1,3,5-Tris(dimethylsilyl)benzene and 2,4,6-Tris(dimethylsilyl)anisole by Beck, H., N., Chaffee, R., G., *J. Chem. Eng. Data* 1963, 8(3), 453-454.

(Poly)halogenated precursors like 1,3,5-Tribromo-benzene and 2,4,6-Tribromo-anisole are commercially available or can be synthesized like 3-Bromo-allyl-benzene and 4-Bromo-allyl-benzene as e.g. described in U.S. Pat. No. 4,788,268 (preparation examples 1, and 2 in columns 6-9) or like e.g. 1,5-Bis(3,5-dichloro-phenoxy)-pentane or 2,2-Bis [3,5-dibromo-4-(3-methylbutyloxy)-phenyl]-propane as described e.g. for similar aryl alkyl ether compounds like Allyl-phenyl-ether or But-2-enyl-(2-methoxy-phenyl)-ether in Houben-Weyl, Methoden der Organischen Chemie, volume VI/3, p 57 (first preparation example) or p 56 (first preparation example), Georg Thieme Verlag, Stuttgart, 1965, 4. edition or like Allyl-(2-chloro-phenyl)-ether as e.g. described by Tarbell, D., S., Wilson, J., W., *J. Am. Chem. Soc.* 1942, 64(5),1066-1070.

Silicon containing components (v) like Chloro-dimethyl-vinyl-silane, Allyl-chloro-dimethyl-silane, Dichloro-dimethyl-silane, Dichloro-methyl-phenyl-silane, Methyl-trichloro-silane, (2-Phenylethyl)-trichloro-silane, or Silicon-tetrachloride are commercially available.

Carbosilane containing component (A) of the inventive composition preferably comprises the following chemical moieties:

Si-Aryl bonds: at least 1, 2, 3 or 4
silicon atoms: at least 1, 2, 3 or 4
unsaturated moieties: at least 2, 3 or 4
Si—Oxygen bonds: none
aromatic moieties: at least 1, 2, 3 or 4
optionally a bisphenol derived spacer moiety.

The amount of carbosilane containing component (A) can be as low as about 1 wt.-%, as low as about 3 wt.-%, or as low as about 10 wt.-% with respect to the cured composition.

The amount of carbosilane containing component (A) can be as high as about 90 wt.-%, as high as about 65 wt.-%, or as high as about 30 wt.-% with respect to the cured composition.

The amount of unsaturated component (B) can be as low as about 1 wt.-%, as low as about 3 wt.-%, or as low as about 10 wt.-% with respect to the cured composition.

The amount of unsaturated component (B) can be as high as about 90 wt.-%, as high as about 65 wt.-%, or as high as about 30 wt.-% with respect to the cured composition.

The amount of initiator (C) can be as low as about 0.00005 wt.-%, as low as about 0.0002 wt.-%, or as low as about 0.002 wt.-% with respect to the cured composition and calculated as elemental metal and related to the overall weight of the material present regarding components (A) to (E).

The amount of initiator (C) can be as high as about 1.0 wt.-%, as high as about 0.5 wt.-%, or as high as about 0.1 wt.-% with respect to the cured composition and calculated as elemental metal and related to the overall weight of the material present regarding components (A) to (E).

The amount of filler (D) can be as low as about 3 wt.-%, as low as about 25 wt.-%, or as low as about 50 wt.-% with respect to the cured composition.

The amount of filler (D) can be as high as about 90 wt.-%, as high as about 80 wt.-%, or as high as about 75 wt.-% with respect to the cured composition.

Optional component (E) can be present up to an amount of about 25 wt.-%, up to about 15 wt.-%, or up to about 3 wt.-% with respect to the cured composition.

The dental composition of the invention meets preferably at least one of the following parameters:

The viscosity of carbosilane containing component (A) usually can be equal or above about 0.1 Pa*s, equal or above about 1 Pa*s, equal or above about 2 Pa*s.

The viscosity of carbosilane containing component (A) usually does not exceed about 40 Pa*s, can be equal or below about 20 Pa*s, or equal or below 5 about Pa*s.

The refractive index of carbosilane containing component (A) usually can be equal or above about 1.510, equal or above about 1.520, or equal or above about 1.530.

The refractive index usually does not exceed about 1.600, can be equal or below about 1.580, or equal or below about 1.560.

The opacity of the cured dental composition usually can be equal or above about 10%, equal or above about 40%, or equal or above about 70%.

The opacity usually does not exceed about 92%, and can be below about 90%, or below about 88%.

The molecular mass (Mw) of carbosilane containing component (A) usually can be equal or above about 250, equal or above about 350, or equal or above about 600.

The molecular mass (Mw) usually does not exceed about 10.000, and can be equal or below about 5.000, or equal or below about 2000.

The compressive strength can be equal or above about 150 MPa, equal or above about 200 MPa, or equal or above about 250 MPa.

The flexural strength usually can be equal or above about 50 MPa, equal or above about 65 MPa, or equal or above about 80 MPa.

If not indicated otherwise, the measurements were done at standard temperature and pressure ("STP", i.e. 23° C. and 1023 hPa) according to the methods described below.

The refractive index of carbosilane containing component (A) can be measured with a Kruess AR 4 D device (refractometer according to Abbe's measure principle). The refractive index is measured at 20.0° C. The refractive index is measured at a wavelength of 589 nm.

The viscosity of carbosilane containing component (A) can be measured with a Haake RotoVisco RV1 device (rotor C60/1 for viscosities up to 8000 mPa*s or rotor C20/1 for viscosities above 8000 mPa*s together with stator P61). The viscosity is measured at 23.0° C. between two plane and parallel plates (i.e. stator and rotor). After activation and rectification of the system, the appropriate rotor is installed. Then the rotor is lowered and the distance between stator and rotor is adjusted to 0.052 mm (using Software RheoWin Pro Job Manager Software Version 2.94} for the viscosity measurement. Then the rotor is lifted and the material to be measured is put on the stator (1.0 ml with rotor C60/1 or 0.04 ml with rotor C20/1). Without undue delay, the rotor is lowered back to the preliminary adjusted measuring position. The material to be measured is tempered at 23.0° C. The shear rate for the measurement is adjusted to a value that produced a torque of at least 5000 μNm (therefore normally shear rates of 100, 200, 500, or 1000 $s^{-1}$ are used depending on the viscosity of the material to be measured). The measurement is started and run for 60 s. The viscosity values (Pa*s) are recorded 20 s after the start of measurement and the mean value of the recorded values is given as viscosity.

The molecular weight ($M_w$) of carbosilane containing component (A) can be determined with GPC. Appropriate methods are know by the expert. In addition the determination of the molecular weight is possible using nuclear magnetic resonance spectroscopy (end-group determination).

The opacity of the cured dental composition can be measured by means of specimens with a defined height of 3.6 (+/−0.1) mm and a diameter of 20 (+/−0.1) mm. These are prepared by filling the material to be measured into suitably high rings, evenly and free of bubbles, and curing it chemically by storing it at standard temperature or 50° C. over night between plane, transparent, silicone oil treated glass slides. The opacity is then measured with the colour measuring device "HunterLab LabScan Spectralcolorimeter" of Hunter Lab Associates Laboratory, Inc., USA (Software SpecWare Software Version 1.01) and given by the device in %-values.

The compressive strength and the flexural strength can be measured comparably to ISO 9917 respectively according to ISO 4049. For the measurement of the compressive strength 10 specimens (3×3×5 mm) of each material are prepared according to the manufacturer's recommendations and the measurements are carried out comparably to ISO 9917 using an universal testing machine (Zwick Z 010, crosshead speed 4mm/min). The compressive strength is given is MPa. The measurement of the flexural strength is carried out according to ISO 4049 using an universal testing machine (Zwick Z 010, crosshead speed 2 mm/min). The flexural strength is given in MPa.

Carbosilane containing component (A) of the inventive composition can be represented by formula (A):

Aryl-[Si(A)$_a$(D-B)$_b$]$_n$       (A)

with independently selected from each other

A=(cyclo)aliphatic moiety ($C_1$ to $C_6$, preferably $C_1$) or aromatic moiety ($C_6$ to $C_{14}$, preferably phenyl);

B=unsaturated moiety (preferably terminal olefinic) attached onto spacer D;

D=spacer=(cyclo)aliphatic moiety (alkadiyl with $C_2$ to $C_{10}$, preferably $C_6$ and $C_9$), wherein C and/or H atoms can be substituted by O, Br, Cl, and Si atoms and which can comprise a bicyclic structural element;

Br=bromine atom;
C=carbon atom;
Cl=chlorine atom;
H=hydrogen atom;
O=oxygen atom;
Si=silicon atom;

Aryl=aromatic moiety (e.g. $C_6$ to $C_{14}$), preferably benzene, naphthalene, alkoxybenzenes, alkoxy naphthalenes, bisphenol A ethers, bisphenol F ethers;
a+b=3;
a=0, 1 or 2 (preferably 2);
b=1, 2 or 3 (preferably 1);
n=1, 2, 3, 4, 5 or 6 (preferably 2 to 4).

Carbosilane containing component (A) can have a comparably high refractive index together with a comparably low viscosity besides a comparably high lipophilicity and a comparably high molecular weight.

Without wishing to be limited to any particular mechanism, it is thought that due to the presence of an aromatic moiety within carbosilane containing component (A) the refractive index and the lipophilicity are comparably high which might be of some importance for dental materials to achieve appropriate esthetics as well as to avoid staining and/or swelling by uptake of water and/or water soluble dyes (e.g. from coffee, tea, red wine).

Depending on the chemical structure of spacer D or the chemical structures of a mixture of different types of spacers D a comparably low viscosity of carbosilane containing component (A) can be adjusted which might be of some importance for dental materials to achieve appropriate handling properties.

Moreover, without wishing to be limited to any particular mechanism, it is thought that due to a comparably high molecular weight of carbosilane containing component (A) and/or different reactivities of used unsaturated moieties B within carbosilane containing component (A) the volume shrinkage of derived dental compositions is reduced in comparison to conventional (meth)acrylate composites.

Spacer D can also comprise a mixture of different types of spacers of similar and/or non similar chemical structure within the same molecule. The use of a mixture of different types of spacers D within the same molecule can be of interest regarding a tailor-made adjustment of viscosity and/or reactivity and/or polarity and/or refractive index of carbosilane containing component (A) as well as of the properties of the cured dental composition like stiffness.

In preferred embodiments carbosilane containing component (A) can be characterized by formulas (I-IV) depending on the molecular structure of carbosilane containing component (A) as well as on the number m of the structural element $\{Aryl-[Si(A)_a(D-B)_b]_n\}_m$ within carbosilane containing component (A).

In a preferred embodiment carbosilane containing component (A) comprises only one aromatic moiety within the molecule in the structural element $\{Aryl-[Si(A)_a(D-B)_b]_n\}_m$ (i.e. m=1) as well as only one Aryl-Si bond (i.e. n=1) and can be characterized by formula (I), wherein the indices are as defined above:

B-D-E- $\{Aryl-[Si(A)_a(D-B)_b]_n\}_m$   (I)

wherein
m=1;
n=1;
E=(cyclo)aliphatic moiety (e.g. alkadiyl with $C_5$ to $C_{11}$, preferably $C_7$ and $C_9$), wherein at least one C atom may be substituted by a Si atom and wherein other C and/or H atoms can also be substituted by O, Br, Cl, and Si atoms, wherein the indices are as defined above.

According to formula (I) the following structural formulas are preferred examples of carbosilane containing component (A)

wherein

D=no spacer or —$(CH_2)$— or —$(CH_2)_4$— or —$(CH_2)_6$— or —$(CH_2)_8$—

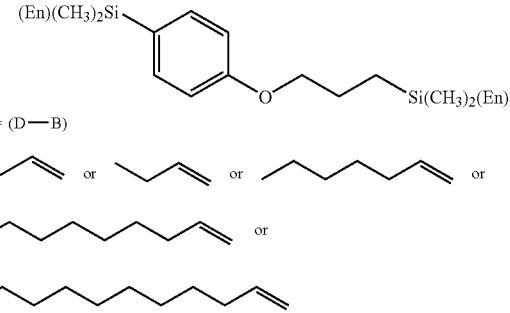

En = (D—B)

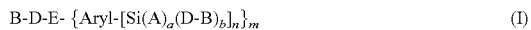

with: A=$C_1$, a=2, b=1, E=$C_7$ with C substituted in part by O and Si, Aryl=phenyl

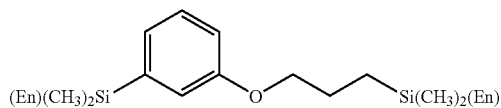

with: A=$C_1$, a=2, b=, E=$C_7$ with C substituted in part by O and Si, Aryl=phenyl

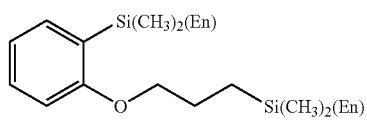

with: A=$C_1$, a=2 b=1, E=$C_7$ with C substituted in part by O and Si, Aryl=phenyl

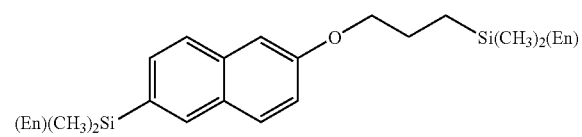

with: A=$C_1$, a=2, b=1, E=$C_7$ with C substituted in part by O and Si Aryl=naphthyl

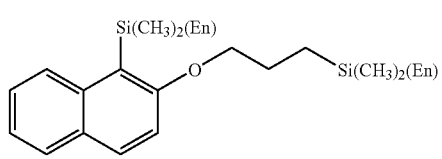

with: A=$C_1$, a=2, b=1, E=$C_7$ with C substituted in part by O and Si, Aryl=naphthyl Carbosilane containing component (A) can be obtained via hydrosilylation reaction according to scheme (I) as described above by reacting a poly Si—H functional carbosilane component (i) with a diolefinic or acetylenic component (ii) using e.g. common noble metal compounds as catalyst.

The following compounds are examples of preferred poly Si—H functional carbosilane components (i) used according to scheme (I) for the synthesis of carbosilane compound (A) fulfilling the requirements according to formula (I):

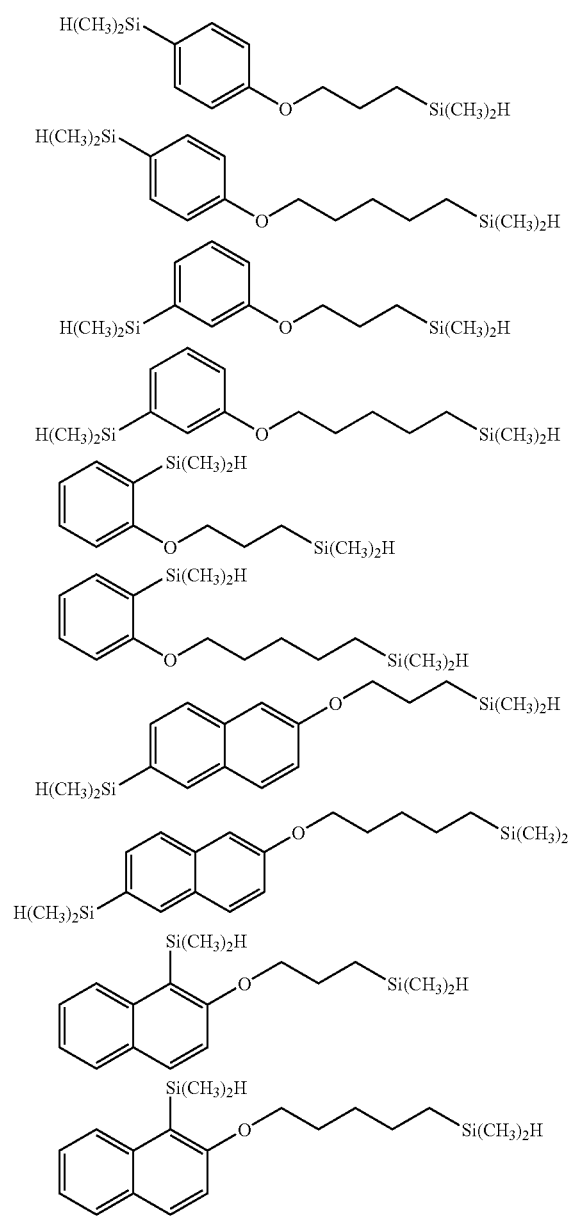

The following compounds are examples of preferred diolefinic or acetylenic components (ii) used according to scheme (I) for the synthesis of carbosilane containing component (A) fulfilling the requirements according to formula (I):

Acetylene

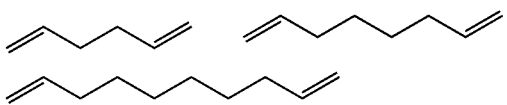

The following compounds are examples of preferred polyhalogenated precursors of metal organic components (iv) used according to scheme (II) for the synthesis of carbosilane containing component (A) via an in situ Grignard reaction fulfilling the requirements according to formula (I):

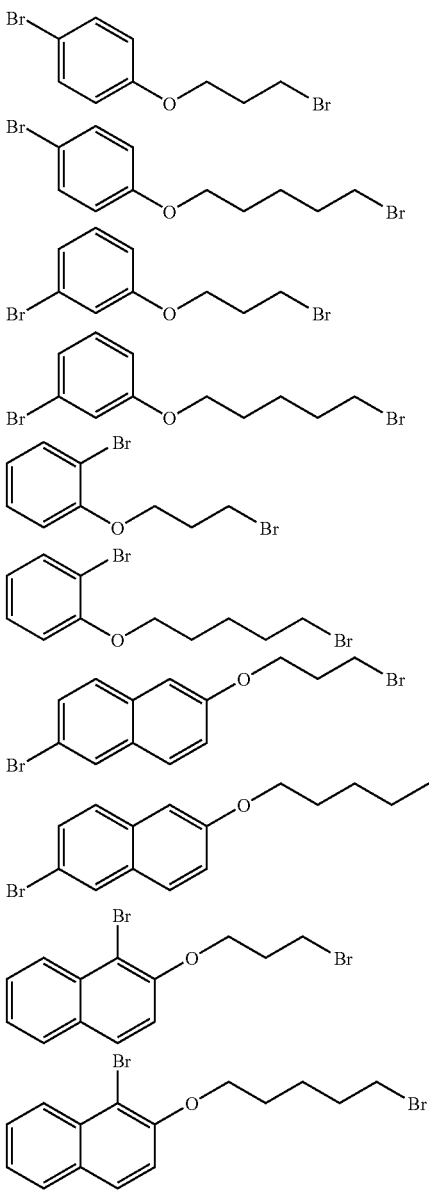

The following compounds are examples of preferred silicon containing components (v) used according to scheme (II) for the synthesis of carbosilane containing component (A) fulfilling the requirements according to general formula (I):

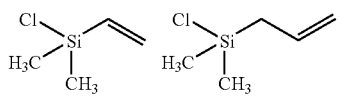

In a further preferred embodiment carbosilane containing component (A) comprises only one aromatic moiety within the molecule in the structural element $\{Aryl\text{-}[Si(A)_a(D\text{-}B)_b]_n\}_m$ (i.e. m=1) as well as more than one Aryl-Si bond (i.e. n≧2) and can be characterized by formula (II), wherein the indices are as defined above:

$$\{Aryl\text{-}[Si(A)_a(D\text{-}B)_b]_n\}_m \quad (II)$$

wherein
m=1
n=2, 3, 4, 5 or 6 (preferably 2 or 3), wherein the indices are as defined above.

According to formula (II) the following structural formulas are preferred examples of carbosilane containing component (A)

wherein

D=no spacer or —(CH$_2$)— or —(CH$_2$)$_4$— or —(CH$_2$)$_6$— or —(CH$_2$)$_8$—

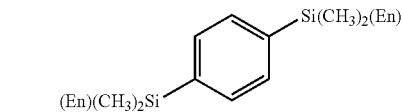

En = (D—B)

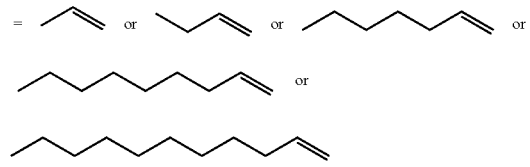

with: A=C$_1$, a=2, b=1, n=2, Aryl=phenyl

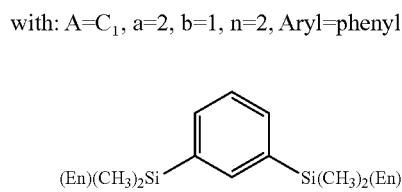

with: A=C$_1$, a=2, b=1, n=2, Aryl=phenyl

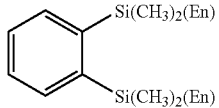

with: A=C$_1$, a=2, b=1, n=2, Aryl=phenyl

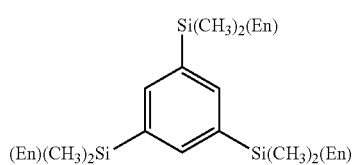

with: A=C$_1$, a=2, b=1, n=3, Aryl=phenyl

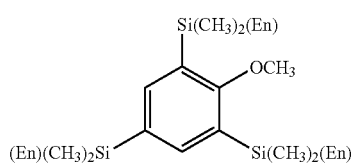

with: A=C$_1$, a=2, b=1, n=3, Aryl=phenyl

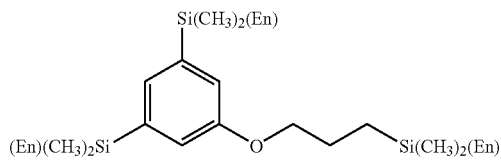

with: A=C$_1$, a=2, b=1, n=2, Aryl=phenyl

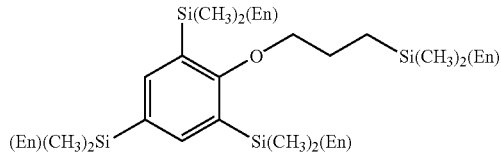

with: A=C$_1$, a=2, b=1, n=3, Aryl=phenyl

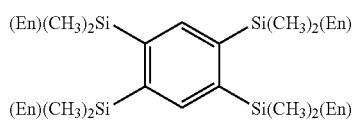

with: A=C$_1$, a=2, b=1, n=4, Aryl=phenyl

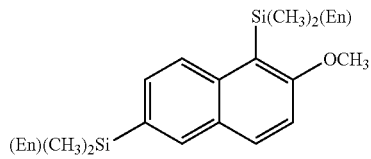

with: A=C₁, a=2, b=1, n=2, Aryl=naphthyl

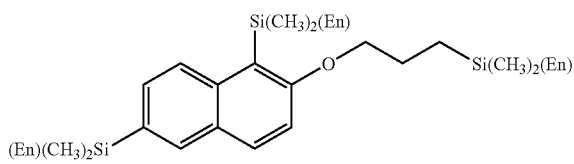

with: A=C₁, a=2, b=1, n=2, Aryl=naphthyl

The following compounds are examples of preferred poly Si—H functional carbosilane components (i) used according to scheme (I) for the synthesis of carbosilane containing component (A) fulfilling the requirements according to formula (II):

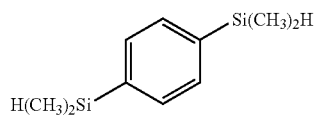

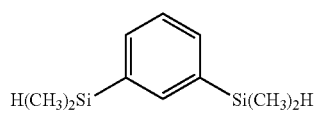

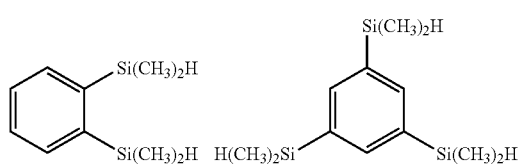

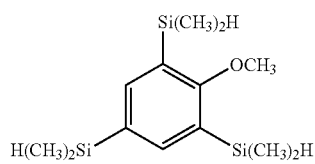

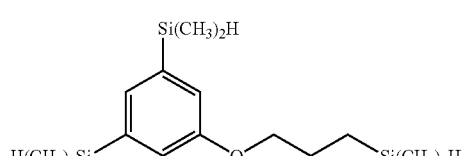

-continued

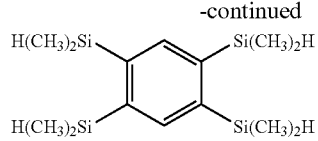

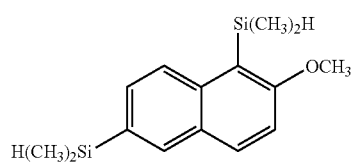

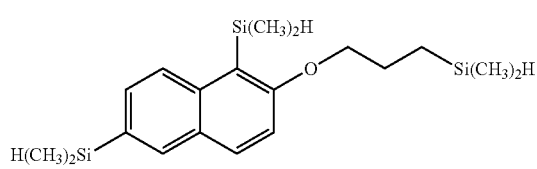

The following compounds are examples of preferred diolefinic or acetylenic components (ii) used according to scheme (I) for the synthesis of carbosilane containing component (A) fulfilling the requirements according to formula (II):

Acetylene

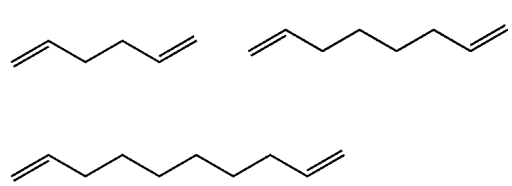

The following compounds are examples of preferred polyhalogenated precursors of possible metal organic components (iv) used according to scheme (II) for the synthesis of carbosilane containing component (A) via an in situ Grignard reaction fulfilling the requirements according to formula (II):

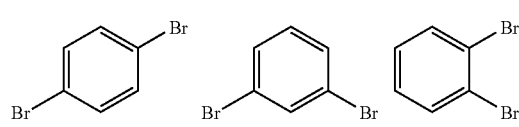

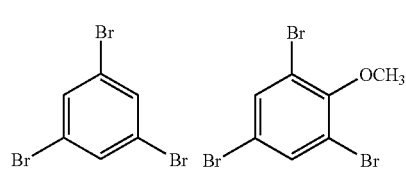

-continued

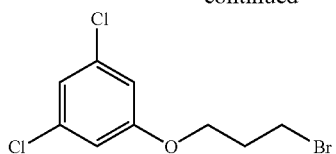

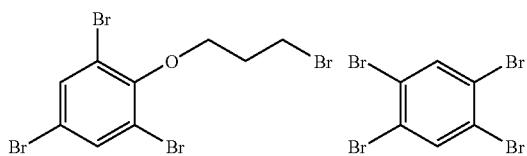

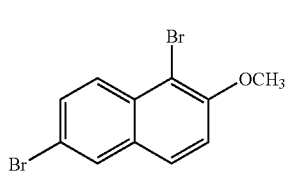

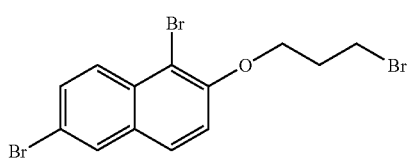

The following compounds are examples of preferred silicon containing components (v) used according to scheme (II) for the synthesis of carbosilane containing component (A) fulfilling the requirements according to formula (II):

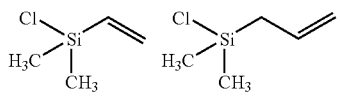

In a further preferred embodiment carbosilane containing component (A) comprises more than one aromatic moiety within the molecule in the structural element $\{Aryl\text{-}[Si(A)_a(D\text{-}B)_b]_n\}_m$ as well as more than one Aryl-Si bond (i.e. the aromatic moieties are always attached to a silicon atom) and can be characterized by formulas (IIIa and IIIb) depending on m (i.e. m≧2 or m=1), wherein the indices are as defined above:

$F\text{-}\{Aryl\text{-}[Si(A)_a(D\text{-}B)_b]_n\}_m$ (IIIa)

with independently selected from each other
m=2, 3 or 4 (preferably 2);
n=1, 2, 3, 4, 5 or 6 (preferably 2 to 4);
F=(cyclo)aliphatic moiety (alkadiyl with $C_0$ to $C_{25}$, preferably $C_0$ to $C_9$) wherein C and/or H atoms can be substituted by O, Br, Cl, and Si atoms, wherein the indices are as defined above.

According to formula (IIIa) the following structural formulas are preferred examples of carbosilane containing component (A)

with independently selected from each other

D=no spacer or —(CH$_2$)— or —(CH$_2$)$_4$— or —(CH$_2$)$_6$— or —(CH$_2$)$_8$—

En = (D—B)

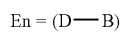

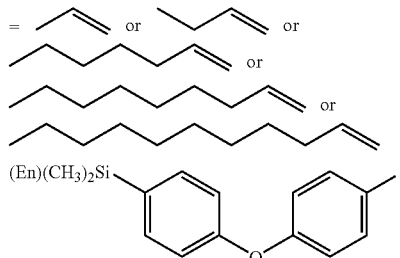

with: A=$C_1$, a=2, b=1, m=2, n=1, F=$C_1$ with C substituted by O, Aryl=phenyl

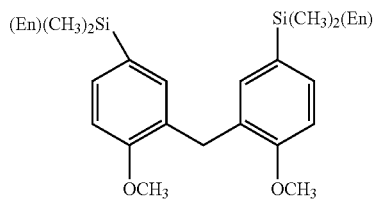

with: A=$C_1$, a=2, b=1, m=2, n=1, F=$C_1$, Aryl=phenyl

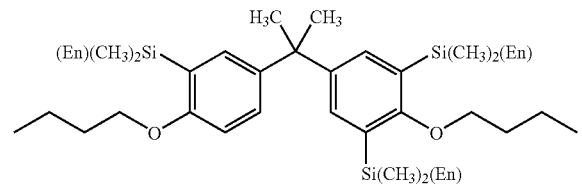

with: A=$C_1$, a=2, b=1, m=2, n=1,2, F=$C_3$, Aryl=phenyl

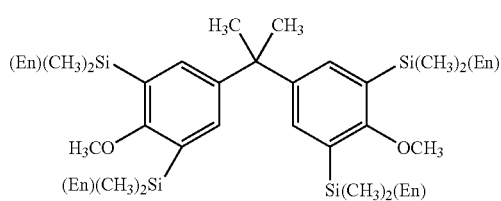

with: A=C$_1$, a=2, b=1, m=2, n=2, F=C$_3$, Aryl=phenyl

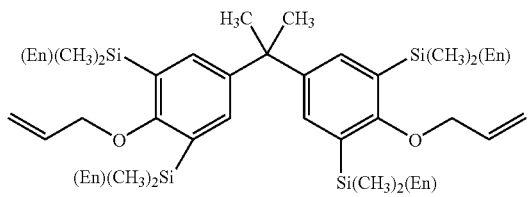

with: A=C$_1$, a=2, b=1, m=2, n=2, F=C$_3$, Aryl=phenyl

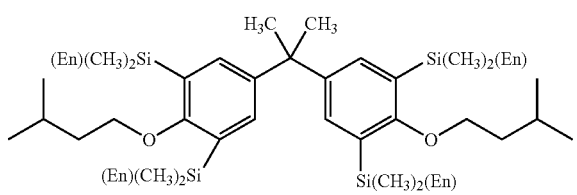

with: A=C$_1$, a=2, b=1, m=2, n=2, F=C$_3$, Aryl=phenyl

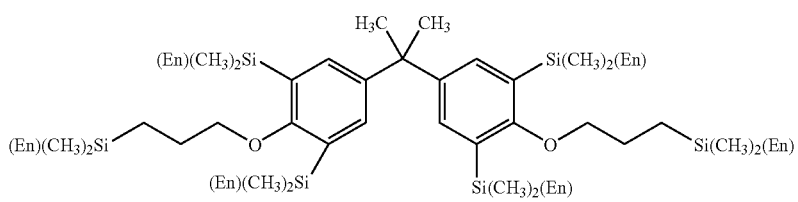

with: A=C$_1$, a=2, b=1, m=2, n=2, F=C$_3$, Aryl=phenyl

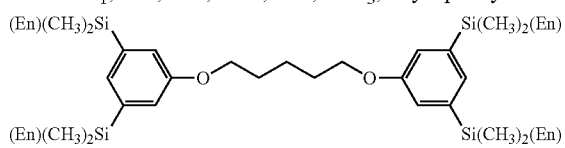

with: A=C$_1$, a=2, b=1, m=2, n=2, F=C$_7$ with C substituted in part by O, Aryl=phenyl with: A=C$_1$, a=2, b=1, m=2, n=2, F=C$_5$ with C substituted in part by O, Aryl=naphthyl

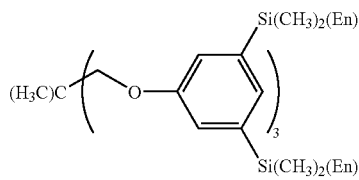

with: A=C$_1$, a=2, b=1, m=3, n=2, F=C$_8$ with C substituted in part by O, Aryl=phenyl

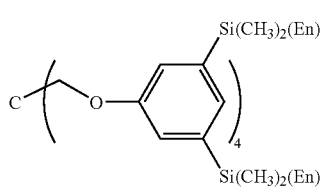

with: A=C$_1$, a=2, b=1, m=4, n=2, F=C$_9$ with C substituted in part by O, Aryl=phenyl The following compounds are examples of preferred poly Si—H functional carbosilane components (i) used according to scheme (I) for the synthesis of carbosilane containing component (A) fulfilling the requirements according to formula (IIIa):

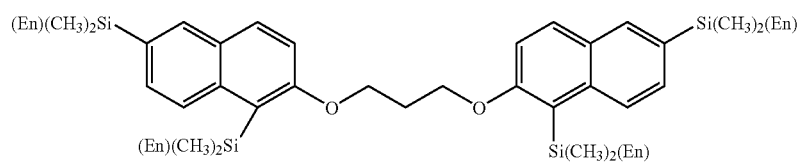

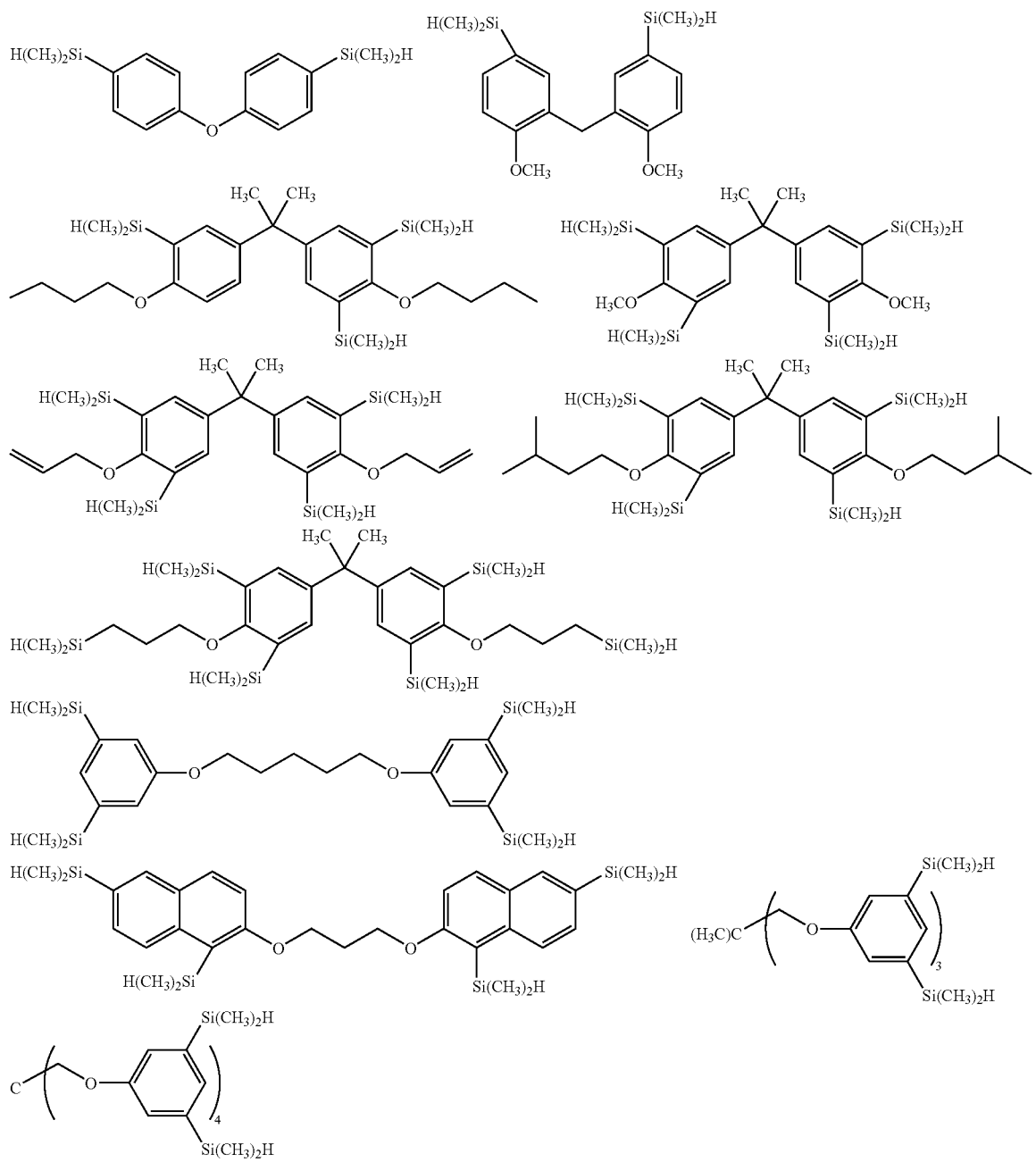

The following compounds are examples of preferred diolefinic or acetylenic components (ii) used according to scheme (I) for the synthesis of carbosilane containing component (A) fulfilling the requirements according to formula (IIIa):

Acetylene

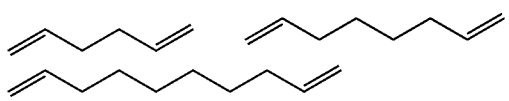

The following compounds are examples of preferred polyhalogenated precursors of metalorganic components (iv) used according to scheme (II) for the synthesis of carbosilane containing component (A) via an in situ Grignard reaction fulfilling the requirements according to formula (IIIa):

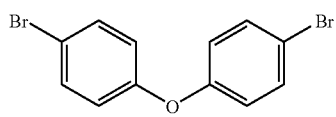

-continued

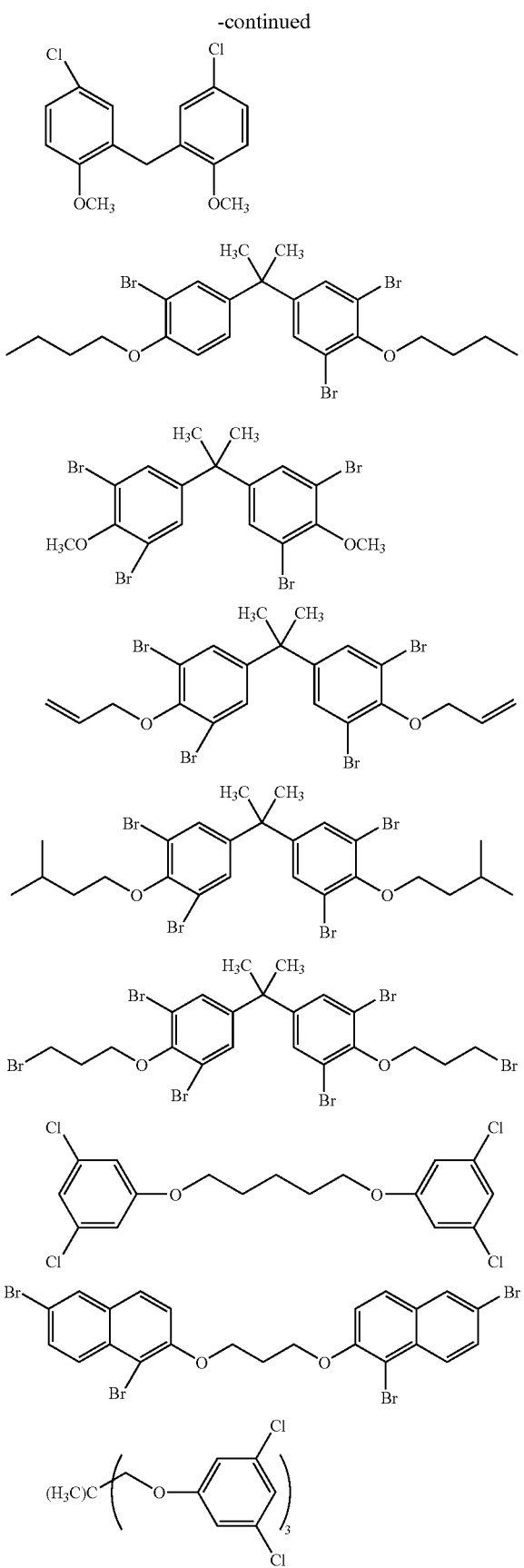

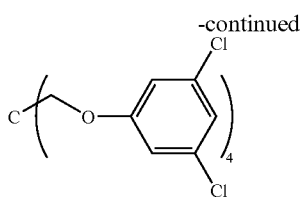

The following compounds are examples of preferred silicon containing components (v) used according to scheme (II) for the synthesis of carbosilane containing component (A) fulfilling the requirements according to formula (IIIa):

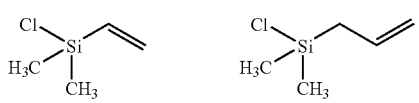

In a further preferred embodiment carbosilane containing component (A) comprises only one silicon atom and more than one aromatic moiety always attached to the silicon atom within the molecule in the structural element Aryl-[Si(A)$_a$(D-B)$_b$]$_n$ (i.e. n=1, b≧1) and can be characterized by formula (IIIb), wherein the indices are as defined above:

$$\text{Aryl-[Si(A)}_a\text{(D-B)}_b\text{]}_n \tag{IIIb}$$

with independently selected from each other
Aryl=allyl-benzene;
A=(cyclo)aliphatic moiety (e.g. $C_1$ to $C_6$, preferably $C_1$) or aliphatic aromatic moiety (e.g. $C_8$ to $C_{16}$, preferably $C_8$ as (2-phenylethyl));
B=unsaturated moiety as terminal $C_2$ based olefinic moiety attached onto a spacer D;
D=spacer=aromatic aliphatic moiety with $C_7$ as α,3/4-toluenediyl with the phenyl ring attached to Si and the methylene group attached to aliphatic olefinic moiety B;
a=0, 1 or 2 (preferably 1 or 2);
b=1, 2 or 3 (preferably 1 or 2);
n=1 wherein the indices are as defined above.

According to formula (IIIb) the following structural formulas are preferred examples of carbosilane containing component (A)

wherein

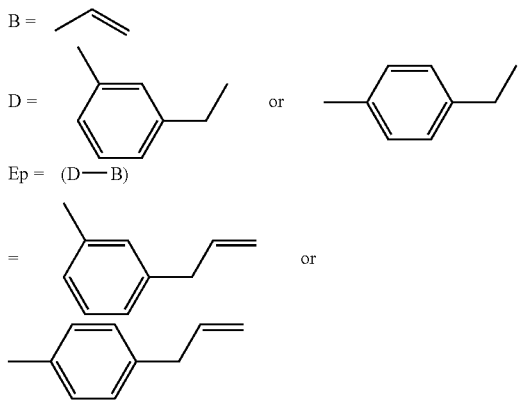

-continued

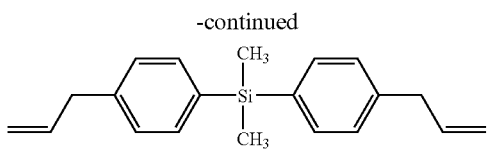

with: A=C$_1$ aliphatic, a=2, b=1, D=α,4-toluenediyl, Aryl=4-allyl-phenyl

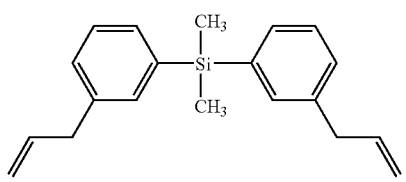

with: A=C$_1$ aliphatic, a=2, b=1, D=α,3-toluenediyl, Aryl=3-allyl-phenyl

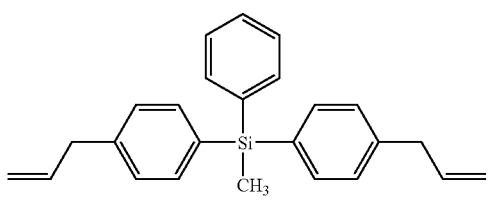

with: A=C$_1$ aliphatic and C$_6$ aromatic, a=2, b=1, D=α,4-toluenediyl, Aryl=4-allyl-phenyl

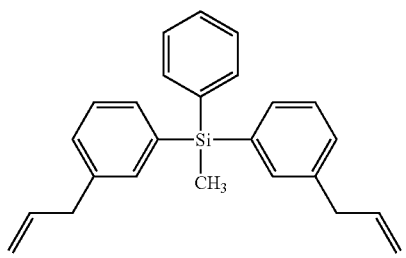

with: A=C$_1$ aliphatic and C$_6$ aromatic, a=2, b=1, D=α,3-toluenediyl, Aryl=3-allyl-phenyl

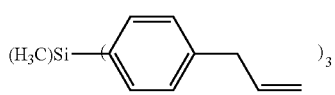

with: A=C$_1$ aliphatic, a=1, b=2, D=α,4-toluenediyl, Aryl=4-allyl-phenyl

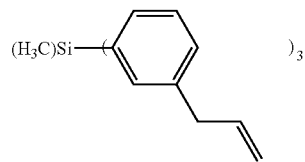

with: A=C$_1$ aliphatic, a=1, b=2, D=α,3-toluenediyl, Aryl=3-allyl-phenyl

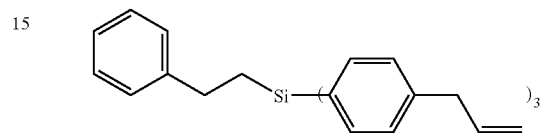

with: A=C$_8$ aliphatic aromatic, a=1, b=2, D=α,4-toluenediyl, Aryl=4-allyl-phenyl

with: A=C$_8$ aliphatic aromatic, a=1, b=2, D=α,3-toluenediyl, Aryl=3-allyl-phenyl

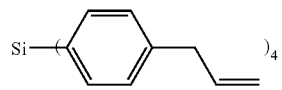

with: a=0, b=3, D=α,4-toluenediyl, Aryl=4-allyl-phenyl

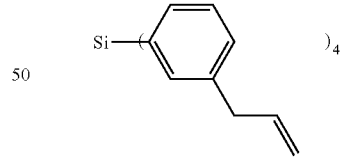

with: a=0, b=3, D=α,3-toluenediyl, Aryl=3-allyl-phenyl

The following compounds are examples of preferred halogenated precursors of metal organic components (iv) used according to scheme (II) for the synthesis of carbosilane containing component (A) via an in situ Grignard reaction fulfilling the requirements according to formula (IIIb):

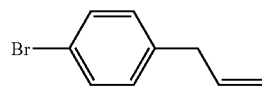

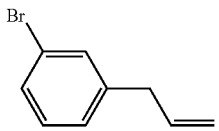

The following compounds are examples of silicon containing components (v) used according to scheme (II) for the synthesis of carbosilane containing component (A) fulfilling the requirements according to formula (IIIb):

(H₃C)₂SiCl₂    (H₃C)SiCl₃

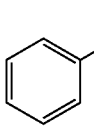  SiCl₄

In a preferred embodiment carbosilane containing component (A) comprises more than one aromatic moiety within the molecule not only in the structural element {Aryl-[Si(A)$_a$(D-B)$_b$]$_n$}$_m$ and can be characterized by formula (IV), wherein the indices are as defined above:

G-{Aryl-[Si(A)$_a$(D-B)$_b$]$_n$}$_m$      (IV)

with independently selected from each other
m=2, 3 or 4 (preferably 2);
n=1, 2, 3, 4, 5 or 6 (preferably 2 to 4);
G=(cyclo)aliphatic or aromatic or (cyclo)aliphatic aromatic or aromatic (cyclo)aliphatic moiety (diyl with C₁ to C₁₀₀, preferably C₃ to C₆₃) wherein C and/or H atoms can be substituted by O, Br, Cl, and Si atoms, wherein the indices are as defined above.

According to formula (IV) the following structural formulas are preferred examples of carbosilane containing component (A):

wherein

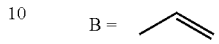

D=no spacer or —(CH₂)— or —(CH₂)₄— or —(CH₂)₆— or —(CH₂)₈—

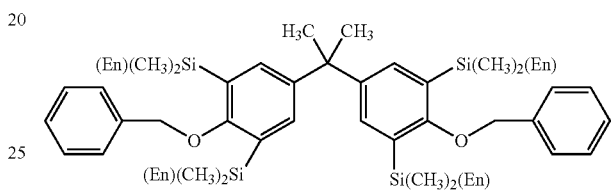

En = (D—B)

with: A=C₁, a=2, b=1, m=2, n=2, G=C₃, Aryl=phenyl

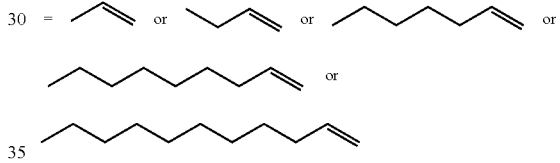

with: A=C₁, a=2, b=1, m=2, n=2, G=C₃, Aryl=phenyl with: A=$C_1$, a=2, b=1, m=2, n=2, G=$C_{10}$ with C substituted in part by O, Aryl=naphthyl The following compounds are examples of preferred poly Si—H functional carbosilane components (i) used according to scheme (I) for the synthesis of carbosilane containing component (A) fulfilling the requirements according to formula (IV):

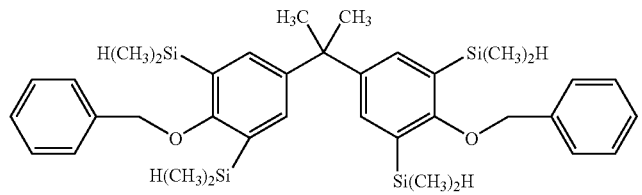

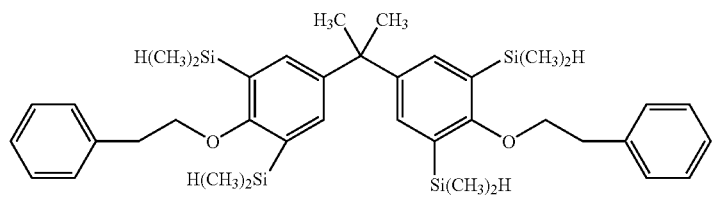

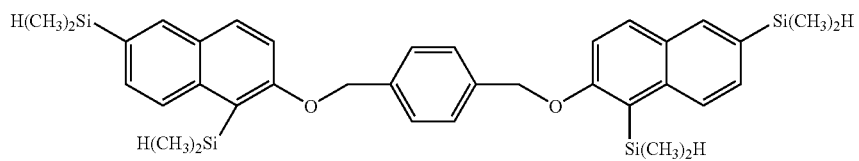

In a more detailed embodiment of formula (IV) carbosilane containing component (A) can be represented by formula (IVa), wherein the indices are as defined above:

with independently selected from each other
p=0, 1, 2, 3 or 4;
o=0, 1, 2, 3, 4 or 5;
Q=H or $CH_3$;
R, S=H, $CH_3$, phenyl or $C_{5-9}$ alkadiyl (e.g. R+S= $(CH_2)_5$, $CH_2$—$CH(CH_3)$—$CH_2$—$CH_2$—$CH_2$, $CH_2$—$CH_2$—CH($CH_3$)—$CH_2$—$CH_2$, $CH_2$—$C(CH_3)_2$—$CH_2$—CH($CH_3$)—$CH_2$);

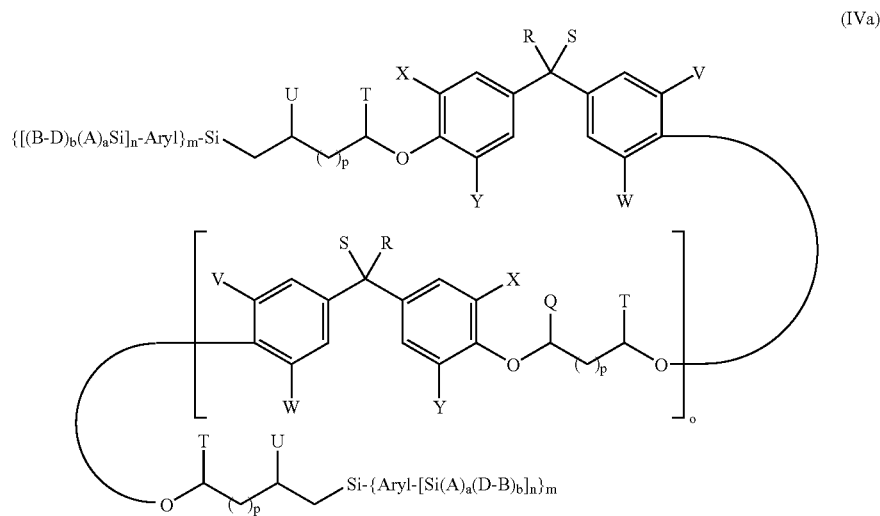

(IVa)

T, U=H or $CH_3$;
V, W, X, Y=H, Br or Cl wherein the indices are as defined above.

According to formula (IVa) the following structural formulas are preferred examples of carbosilane containing component (A)

wherein

B = 

D=no spacer or —$(CH_2)$— or —$(CH_2)_4$— or —$(CH_2)_6$— or —$(CH_2)_8$—

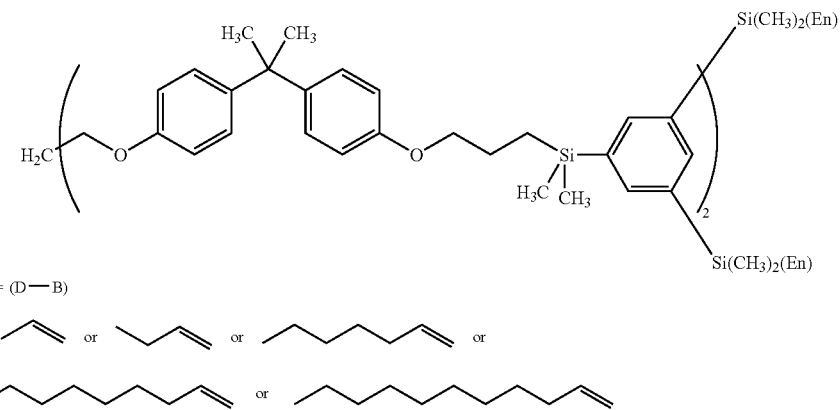

with: A=$C_1$, a=2, b=1, m=2, n=2, G=$C_{49}$ with C substituted in part by O and Si, Aryl=phenyl

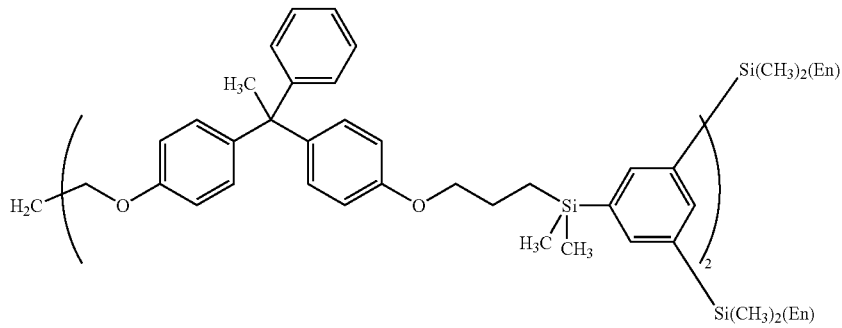

with: A=$C_1$, a=2, b=1, m=2, n=2, G=$C_{59}$ with C substituted in part by O and Si, Aryl=phenyl

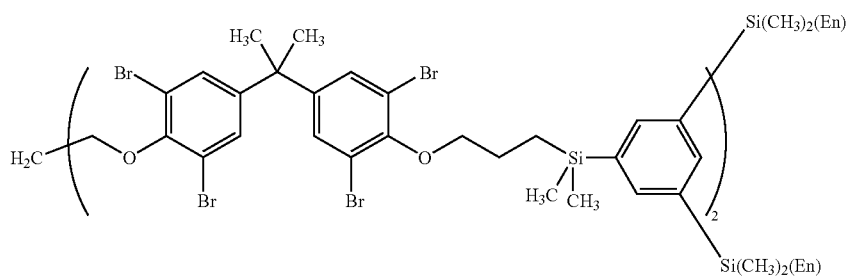

with: A=$C_1$, a=2, b=1, m=2, n=2, G=$C_{57}$ with C substituted in part by Br, O, and Si, Aryl=phenyl

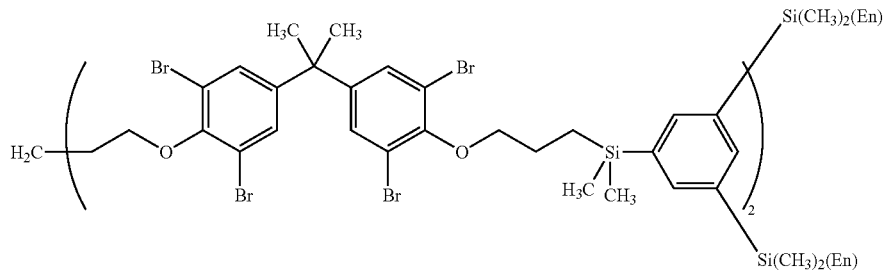

with: A=$C_1$, a=2, b=1, m=2, n=2, G=$C_{63}$ with C substituted in part by Br, O, and Si, Aryl=phenyl In another more detailed embodiment carbosilane containing component (A) can be represented by formula (IVb), wherein the indices are as defined above:

(IVb)

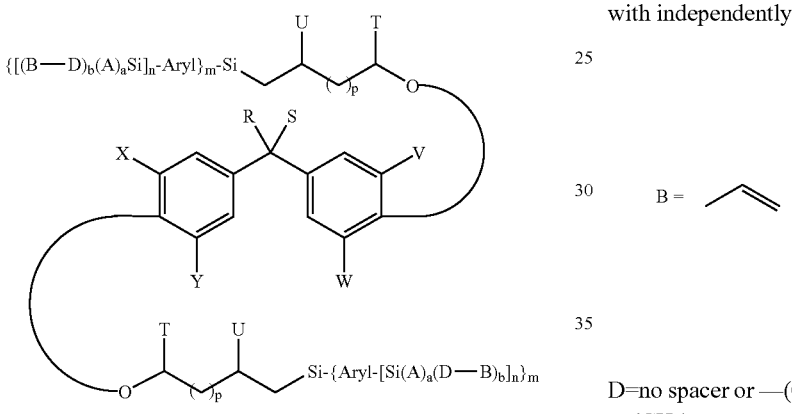

According to formula (IVb) the following structural formulas are preferred examples of carbosilane containing component (A)

with independently selected from each other

B = /\

D=no spacer or —($CH_2$)— or —($CH_2$)$_4$— or —($CH_2$)$_6$— or —($CH_2$)$_8$—

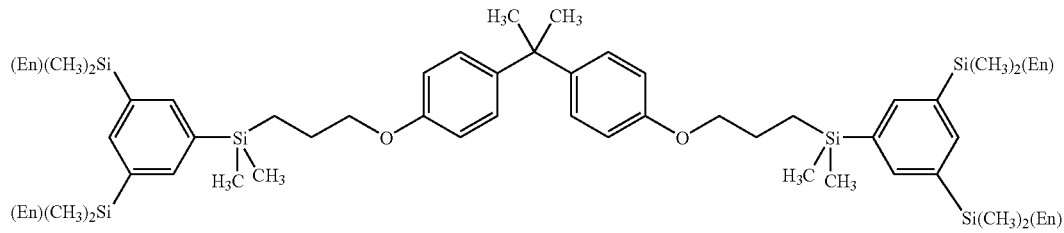

En = (D—B)

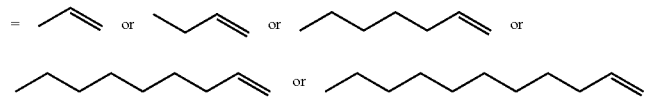

with: A=$C_1$, a=2, b=1, m=2, n=2, G=$C_{29}$ with C substituted in part by O and Si, Aryl=phenyl

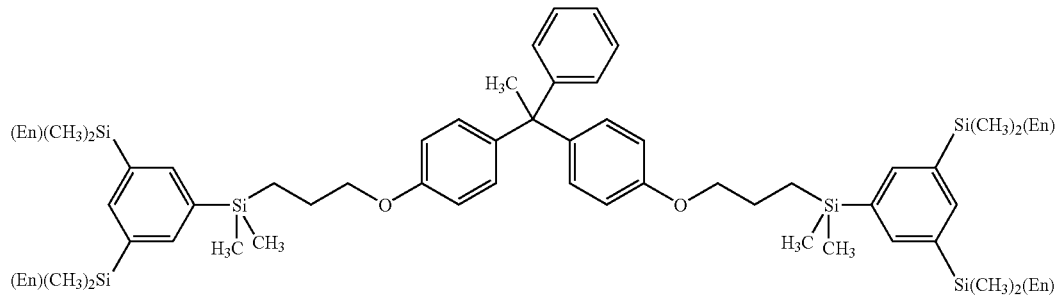

with: A=$C_1$, a=2, b=1, m=2, n=2, G=$C_{34}$ with C substituted in part by O and Si, Aryl=phenyl

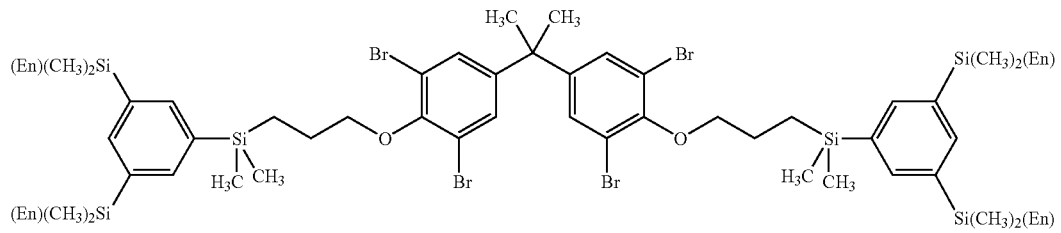

with: A=$C_1$, a=2, b=1, m=2, n=2, G=$C_{33}$ with C substituted in part by Br, O, and Si, Aryl=phenyl

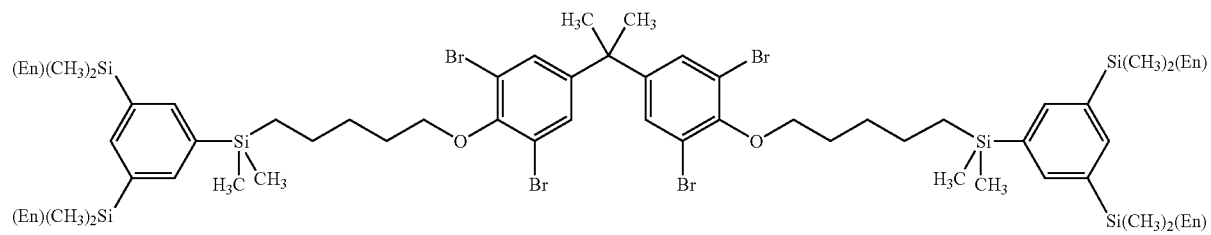

with: A=$C_1$, a=2, b=1, m=2, n=2, G=$C_{37}$ with C substituted in part by Br, O, and Si, Aryl=phenyl The following compounds are examples of preferred poly Si—H functional carbosilane components (i) used according to scheme (I) for the synthesis of carbosilane containing component (A) fulfilling the requirements according to formulas (IVa, and IVb):

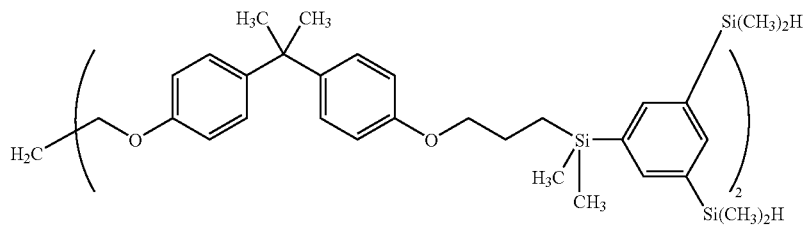

-continued
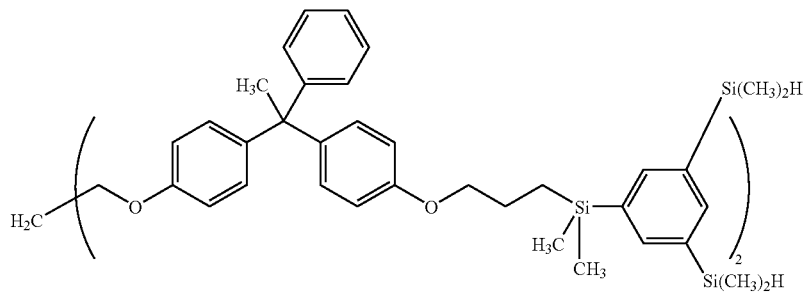
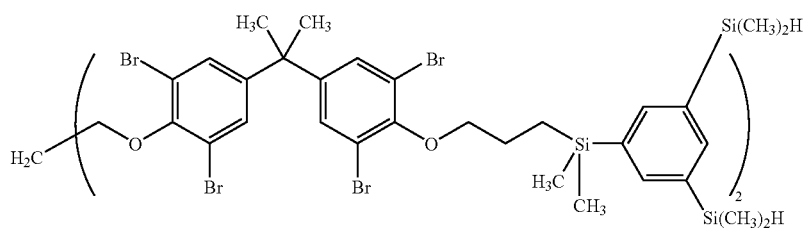
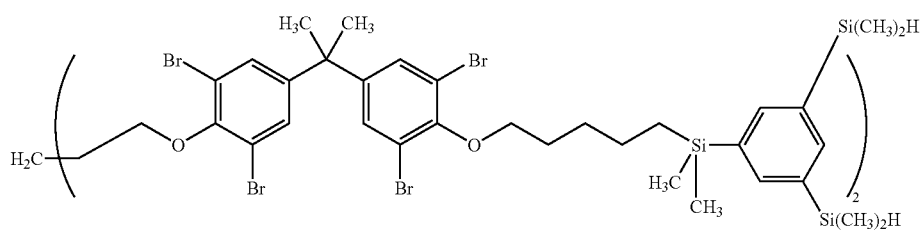
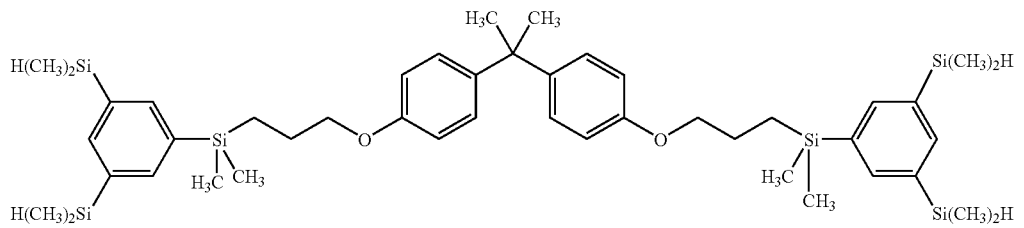
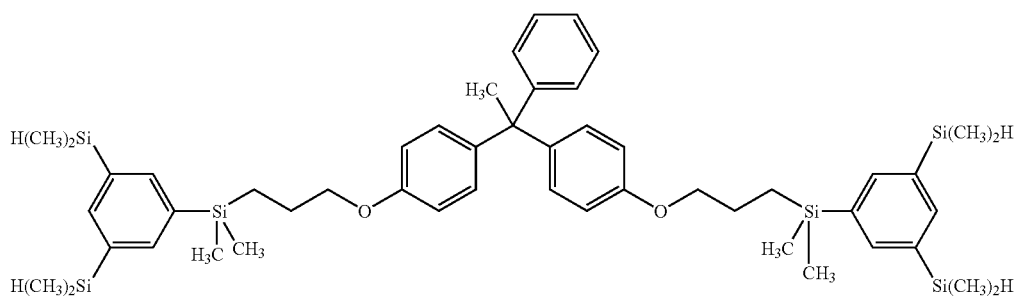
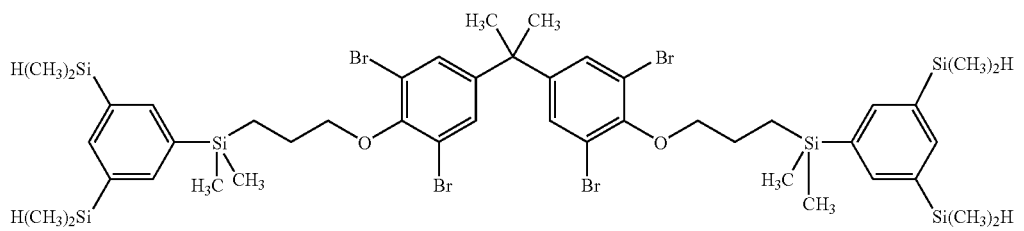

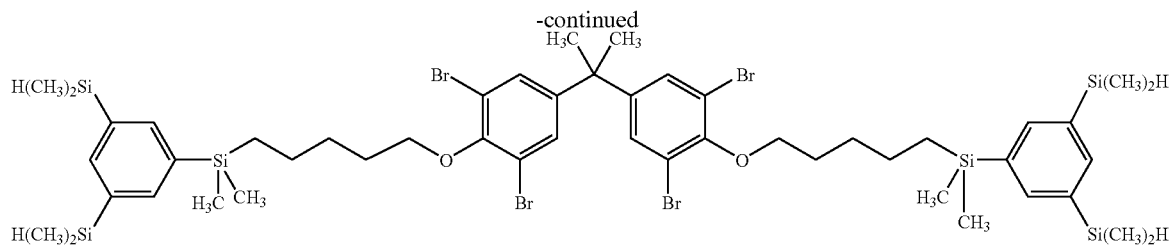
These preferred poly Si—H functional carbosilane components (i) can be synthesized e.g. via a hydrosilylation reaction of non silicon containing diolefinic precursor (ia) and poly Si—H functional carbosilane component (ib) used according to scheme (I) for the synthesis of a Si—H compound (i).
Examples of non silicon containing diolefinic precursors (ia) are:
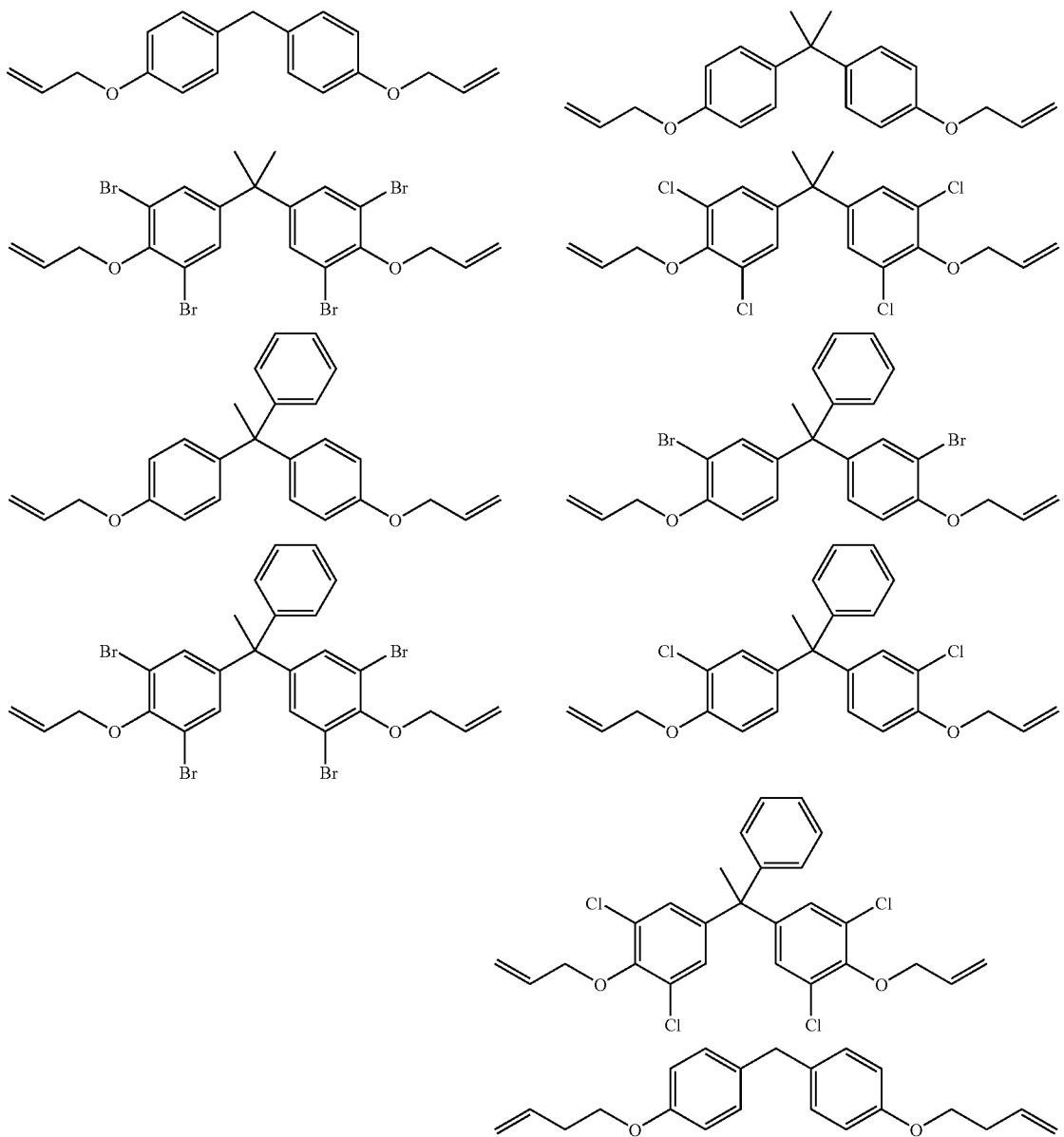

-continued
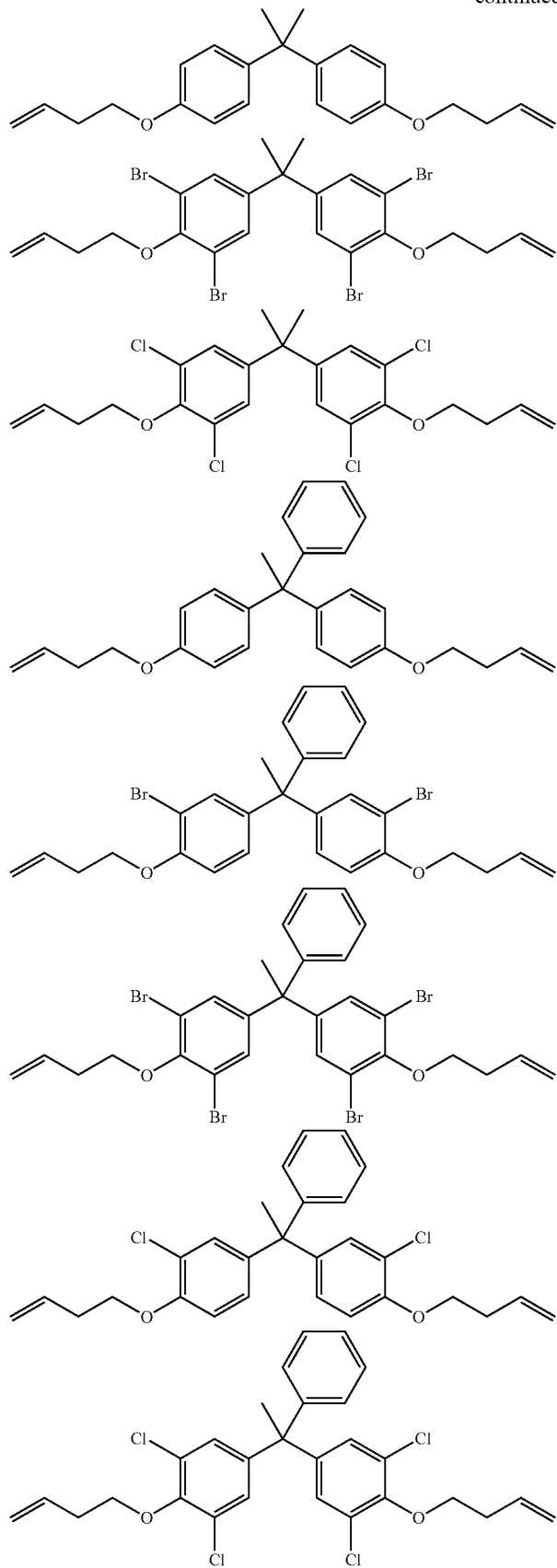

-continued
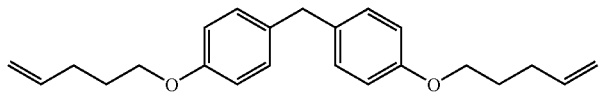
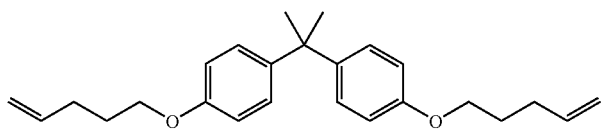
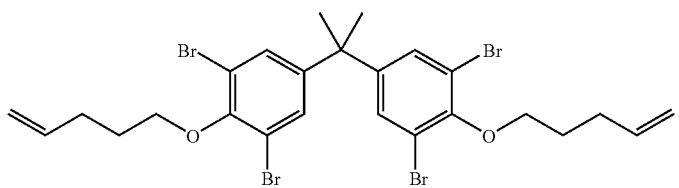
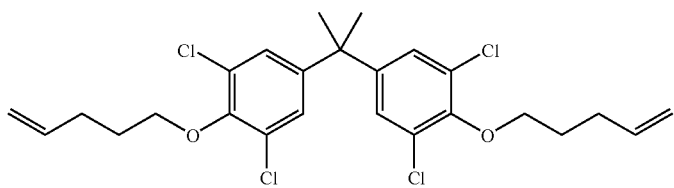
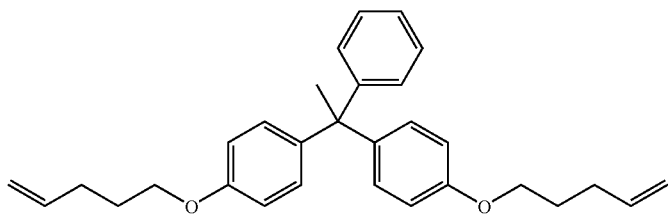
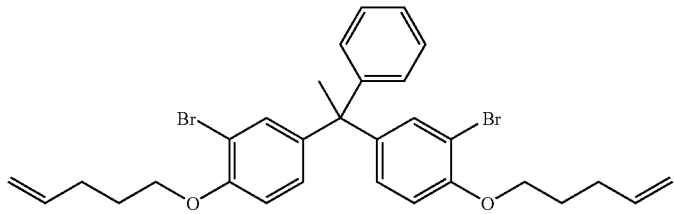
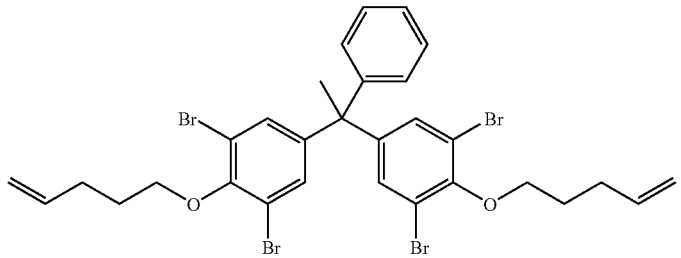
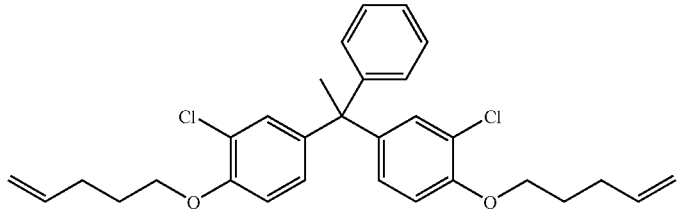

-continued
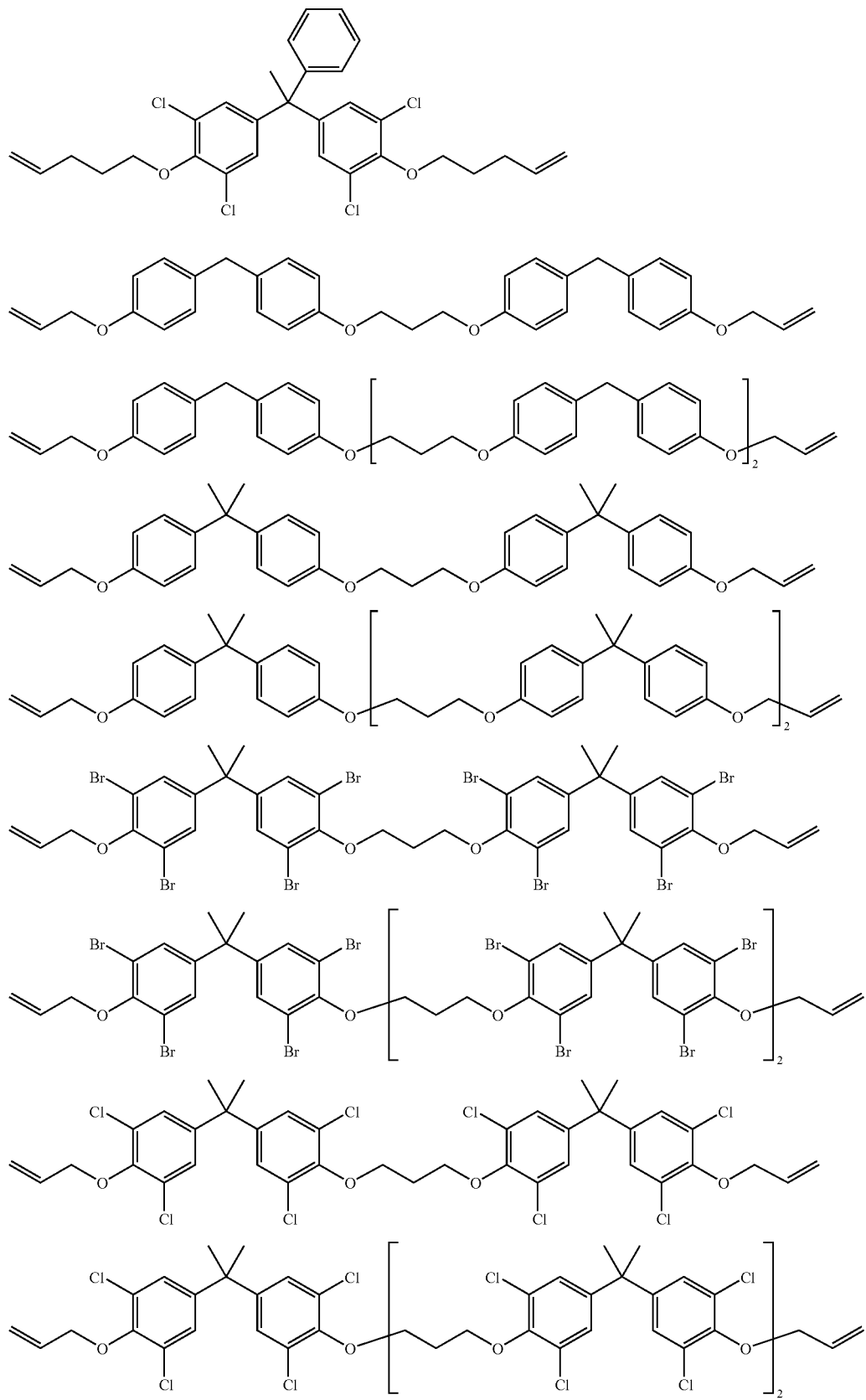

-continued
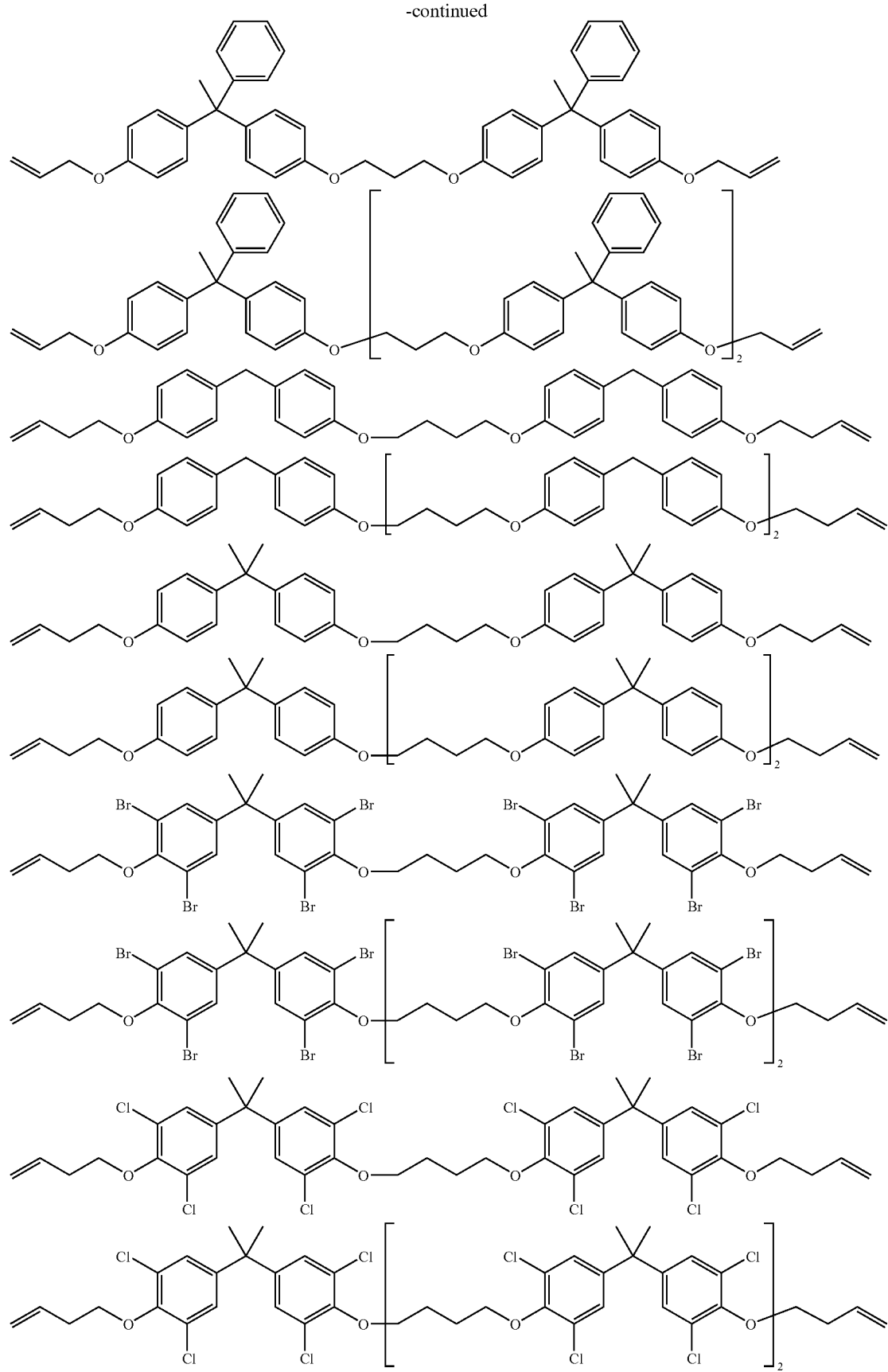

-continued
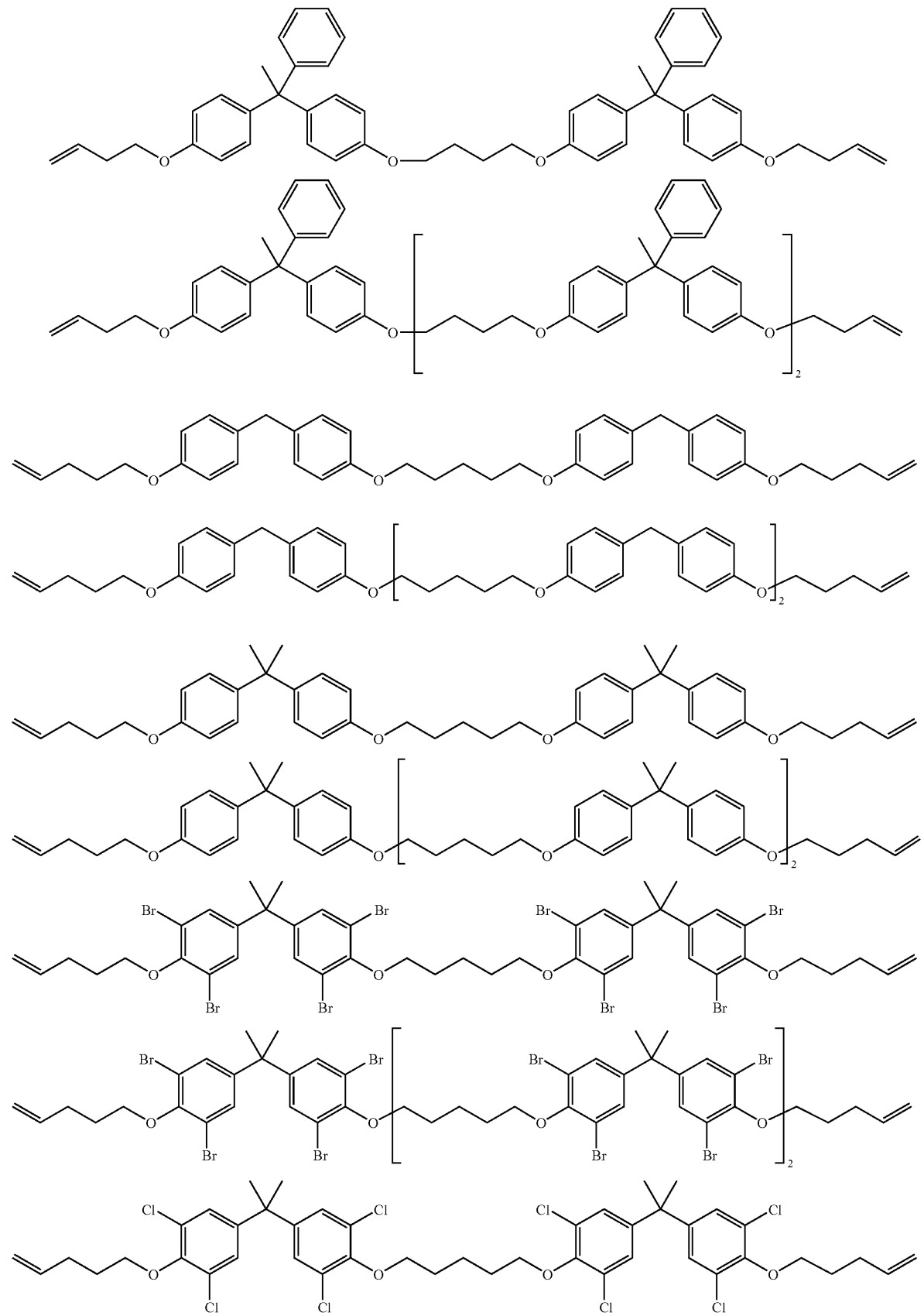

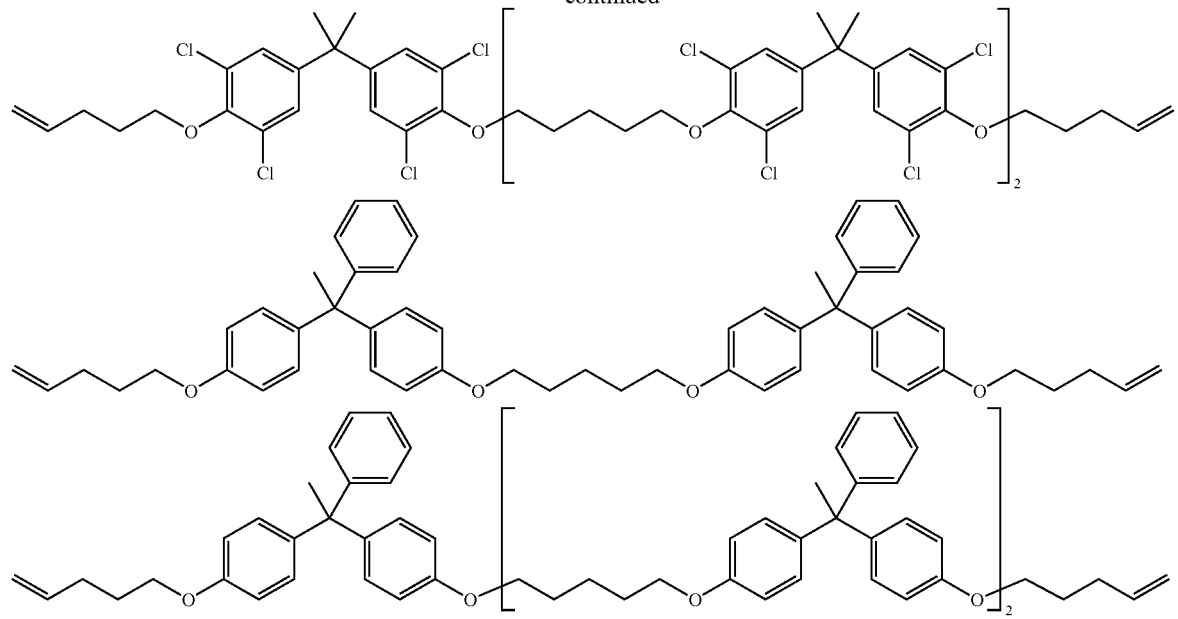

Examples of preferred poly Si—H functional carbosilane components (ib) are:

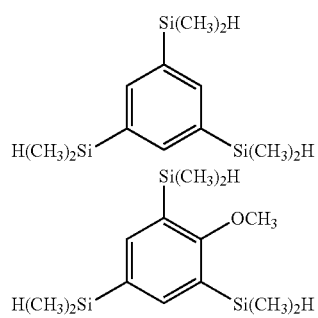

The following compounds are examples of preferred diolefinic or acetylenic components (ii) used according to scheme (I) for the synthesis of carbosilane containing component (A) fulfilling the requirements according to formulas (IV, IVa, and IVb):

Acetylene

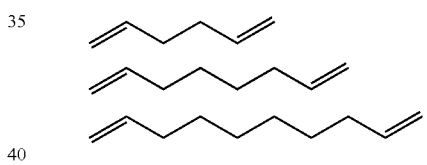

The following compounds are examples of preferred polyhalogenated precursors of metal organic components (iv) used according to scheme (II) for the synthesis of carbosilane containing component (A) via an in situ Grignard reaction fulfilling the requirements according to formula (IV):

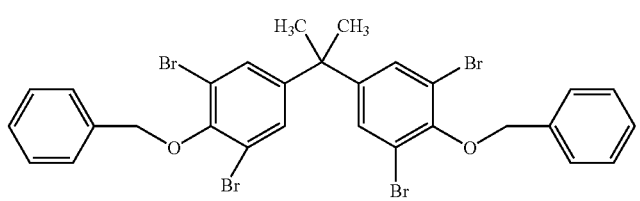

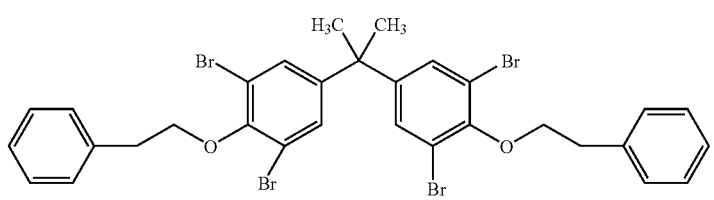

-continued

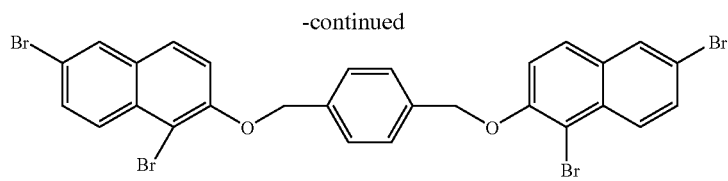

The following compounds are examples of preferred silicon containing components (v) used according to scheme (II) for the synthesis of carbosilane containing component (A) fulfilling the requirements according to formula (IV):

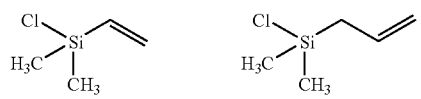

Useful Si—H functional compounds (B) can react with carbosilane containing component (A) via hydrosilylation reaction. Such a Si—H functional compound (B) include organopolysiloxane and/or carbosilane derived compound with Si-bonded hydrogen atoms. Si—H functional compound (B) is preferably an organopolysiloxane with at least 2 Si-bonded hydrogen atoms per molecule and/or a carbosilane with at least 2 Si-bonded hydrogen atoms per molecule.

Useful initiators (C) can initiate curing of carbosilane containing component (A) of the composition in the presence of a Si—H functional compound (B).

Such initiators can be light curing or chemical curing. Both types of initiators are well known to the skilled person in the art.

Representative examples of such initiators include, e.g. complexes of platinum (oxidation states 0 and/or +2), palladium (oxidation states 0 and/or +2), or rhodium (oxidation states 0 and/or +1), as described e.g. within Marciniec, B., Comprehensive Handbook on Hydrosilylation, p 8ff., Pergamon Press, Oxford, 1992 or e.g. in U.S. Pat. Nos. 5,145,886, 6,046,250, 6,376,569.

Initiator (C) is preferably a platinum complex which was prepared from hexachloroplatinum acid by reduction with tetramethyldivinyldisiloxane. These compounds are known. Other platinum compounds which can accelerate addition cross-linking, are also suitable. Examples of suitable Platinum-siloxane complexes are described e.g. in U.S. Pat. Nos. 3,715,334, 3,775,352 and 3,814,730. The platinum catalyst is preferably used in quantities of 0.00005 to 0.5 wt.-%, particularly 0.0002 to 0.2 wt.-%, each calculated as elemental platinum and related to the overall weight of the material present regarding components (A) to (E).

To control the reactivity, it may be desirable to add an inhibitor which prevents premature cross-linking to elastomers. Such inhibitors are known and described, e.g. in U.S. Pat No. 3,933,880. Examples of such include acetylenic unsaturated alcohols such as 3-Methyl-1-butyne-3-ol, 1-Ethynylcyclohexane-1-ol, 3,5-Dimethyl-1-hexyne-3-ol and 3-Methyl-1-pentyne-3-ol. Examples of inhibitors based on vinyl siloxane include 1,1,3,3-Tetramethyl-1,3-divinyl siloxane and poly-, oligo- and disiloxane-containing vinyl groups.

The composition of the invention may also include filler (D), preferably inorganic fillers like quartz, ground glasses, silica gels as well as pyrogenic silicic acids and precipitation silicic acids or their granules. X-ray-opaque fillers are also preferably used, at least partially. These can, for example, be X-ray-opaque glasses, i.e. glasses which, for example, contain strontium, barium or lanthanum (e.g. according to U.S. Pat. No. 3,971,754) Some of the fillers may contain an X-ray-opaque additive, such as yttrium trifluoride, strontium hexafluorozirconate or fluorides of the rare earth metals (e.g. according to EP 0 238 025 A1). For better incorporation into the polymer matrix, it may be advantageous to hydrophobize the inorganic fillers. Typical hydrophobization agents include silanes, e.g. (5-Hexenyl)trimethoxysilane or [2-(3-Cyclohexenyl)ethyl]trimethoxysilane. The fillers preferably have an average grain size <20 µm, particularly <5 µm and more particularly <2 µm and an upper grain limit of 150 µm, particularly 70 µm and more particularly 25 µm. Such fillers can be present in amounts of from about 3 to about 90 weight percent, especially about 25 to about 80 or about 50 to about 75 wt.-% of the composition.

Non-reinforcing fillers may also be used in the invention such as quartz, cristobalite, calcium silicate, diatomaceous earth, zirconium silicate, montmorillonite such as bentonite, zeolite, including moleculer sieves such as sodium aluminium silicate, metal oxide powder such as aluminium or zinc oxide or their mixed oxides, barium sulphate, calcium carbonate, plaster, glass and plastic powder.

Suitable fillers also include reinforcing fillers such as e.g. pyrogenic or precipitated silicic acid and silica aluminium mixed oxides. The above mentioned fillers can be hydrophobized, for example by treatment with organosilanes or siloxanes or by the etherification of hydroxyl groups to alkoxy groups. One type of filler or also a mixture of at least two fillers can be used.

A combination of reinforcing and non-reinforcing fillers is particularly preferred. In this respect, the quantity of reinforcing fillers can vary from about 1 to about 10 wt.-%, and in particular, from about 2 to about 5 wt.-%.

The difference in the named overall ranges, i.e. about 2 to about 89 wt.-% is accounted for by non-reinforcing fillers.

Pyrogenically-prepared highly-disperse, silicic acids which have preferably been hydrophobized by surface treatment are preferred as reinforcing fillers. The surface treatment can be carried out, e.g. with dimethyldichlorosilane, hexamethyldisilazane, tetramethylcyclotetrasiloxane or polymethylsiloxane.

Particularly preferred non-reinforcing fillers are quartzes, cristobalites, calcium carbonate and sodium aluminium silicates which can be surface-treated. The surface treatment can generally be carried out with the same methods as described in the case of the strengthening fillers.

Optionally additives (E) like stabilizers, modifiers, dyes, pigments, thixotropic agents, flow improvers, or thinning agents, polymeric thickeners, surfactants, and diluting agent(s) can be added alone or in admixture.

The above described carbosilane containing component (A) can be used as monomer in dental compositions that are curable preferably via hydrosilylation reaction of unsaturated groups, especially terminal olefinic groups.

The dental composition of the invention can be used e.g. as dental filling materials, crown and bridge materials, veneer materials, inlays or onlays.

Carbosilane containing component (A) can be used for preparing a dental material in a process comprising the steps of
a) providing a dental composition containing carbosilane containing component (A);
b) applying the dental composition to a surface;
c) curing the dental composition.

The surface is usually a surface of a tooth, a crown or a bridge.

The dental compositions can be provided as a 1 part mixture or as a 2 part mixture. This usually depends on the initiator used. If the initiator is light curing, the dental composition can be provided as a 1 part mixture, if the initiator is redox curing, the dental composition should be provided as a 2 part mixture.

Therefore, the invention also relates to a kit of parts, comprising a base part (I) and a catalyst part (II), wherein the base part (I) comprises carbosilane containing component (A), Si—H functional component (B), and filler (D), and the catalyst part (II) comprises initiator (C), and wherein component (E) is present either in the base part or the catalyst part or in the base part and the catalyst part.

The dental compositions of the invention is usually packaged in a container or cartridge, preferably in a dental compule. Examples of such computes are described in U.S. Pat. Nos. 5,322,440 or 4,391,590 or 5,165,890.

The invention also relates to a method of producing a curable dental composition comprising the steps
a) providing components (A), (B), (C), optionally (D) and optionally (E);
b) mixing the components of step a), wherein component (A) is obtainable via hydrosilylation reaction or obtainable via Grignard reaction or in situ Grignard reaction.

The Grignard reaction or in situ Grignard reaction comprises reacting (poly)organometallic functional component (iv) or (poly)halogenated precursor and silicon containing component (v) as describe above.

The hydrosilylation reaction comprises reacting poly Si—H functional carbosilane component (i) and diolefinic or acetylenic component (ii) as describe above.

The invention is hereinafter described by examples. The examples are for illustrative purpose only and not intended to limit the invention.

The compounds listed in table 1 were prepared according to the references listed above and their refractive index and viscosity measured.

TABLE 1

| Examples of Compounds | Refractive Index | Viscosity [mPa * s] | Molecular Weight [g/mol] |
|---|---|---|---|
| Reference Compound 1: 1,3,5,7-Tetramethyl-cyclotetrasiloxane | 1.387 | 200 | 240.5 |
| Reference Compound 2: 1,3,5,7-Tetramethyl-1,3,5,7-tetravinyl-cyclotetrasiloxane | 1.434 | 400 | 344.7 |
| Example Compound 1: Bis(4-allyl-phenyl)-dimethyl-silane | 1.556 | 9 | 292.5 |
| Example Compound 2: 2,2-Bis[3,5-bis(dimethyl-vinyl-silyl)-4-allyloxy-phenyl]-propane | 1.557 | 13700 | 645.2 |

Dental compositions containing carbosilane compounds according to the invention as well as dental compositions containing state of the art reference compounds were prepared and their opacity measured.

TABLE 2

| Amounts in %-Weight | Examples of Dental Compositions | | |
|---|---|---|---|
| | 1 | 2 | 3 |
| Reference Compound 1 | 20.3 | 17.1 | 15.9 |
| Reference Compound 2 | 30.5 | | |
| Example Compound 1 | | 41.5 | |
| Example Compound 2 | | | 42.7 |
| (1,3,5,7-Tetramethyl-1,3,5,7-tetravinyl)platinum(0) | 1.4 | 1.4 | 1.4 |
| Quartz, mean particle size < 2 µm | 30.4 | 35.0 | 35.0 |
| Hydrophobized Highly-Disperse Silicic Acid | 17.4 | 5.0 | 5.0 |
| Opacity [%] | 95.6 | 81.3 | 86.2 |
| Exact Height of Specimen [mm] | (3.6) | (3.6) | (3.6) |

The invention claimed is:
1. A dental composition comprising:
an Si—H functional component;
an initiator; and
a carbosilane component represented by formula (1):

Aryl-[Si(A)$_a$(D-B)$_b$]$_n$     (1)

wherein, independently selected from each other,
A is an aliphatic or cycloaliphatic moiety ($C_1$ to $C_6$) or aromatic moiety ($C_6$ to $C_{14}$);
B is an unsaturated moiety attached onto a spacer D;
D is a spacer having a (cyclo)aliphatic moiety wherein C and/or H atoms can be substituted by O, Br, Cl, and Si atoms and which can comprise a bicyclic structural element;
Br is a bromine atom;
C is a carbon atom:
Cl is a chlorine atom;
H is a hydrogen atom;
O is an oxygen atom,
Si is a silicon atom;
Aryl is an aromatic moiety;
a+b is 3;
a is 0, 1 or 2;
b is 1, 2 or 3; and
n is 1, 2, 3, 4, 5 or 6.
2. The dental composition of claim 1, wherein the carbosilane containing component is represented by the following formula (I):

B-D-E-{Aryl-[Si(A)$_a$(D-B)$_b$]$_n$}$_m$     (I)

wherein, independently selected from each other,
a is 0, 1 or 2;
b is 1, 2 or 3;
m is 1;
n is 1;
A is an aliphatic or cycloaliphatic moiety ($C_1$ to $C_6$) or aromatic moiety ($C_6$ to $C_{14}$);
B is an unsaturated moiety attached onto a spacer D;
D is a spacer having a (cyclo)aliphatic moiety wherein C and/or H atoms can be substituted by O, Br, Cl, and Si atoms and which can comprise a bicyclic structural element;
E is a (cyclo)aliphatic moiety, wherein at least one C atom may be substituted by a Si atom and wherein other C and/or H atoms can be substituted by O, Br, Cl, and Si atoms; and
Aryl is an aromatic moiety.

3. The dental composition of claim 1, wherein the carbosilane containing component is represented by the following formula (II):

(II)

wherein, independently selected from each other,
A is an aliphatic or cycloaliphatic moiety ($C_1$ to $C_6$) or aromatic moiety ($C_6$ to $C_{14}$);
B is an unsaturated moiety attached onto a spacer D;
D is a spacer having a (cyclo)aliphatic moiety wherein C and/or H atoms can be substituted by O, Br, Cl, and Si atoms and which can comprise a bicyclic structural element;
a is 0, 1 or 2;
b is 1, 2 or 3;
m is 1;
n is 2, 3, 4, 5 or 6; and
Aryl is an aromatic moiety.

4. The dental composition of claim 1, wherein the carbosilane containing components is represented by the following formula (IIIa):

(IIIa)

wherein, independently selected from each other,
A is an aliphatic or cycloaliphatic moiety ($C_1$ to $C_6$) or aromatic moiety ($C_6$ to $C_{14}$);
B is an unsaturated moiety attached onto a spacer D;
D is a spacer having a (cyclo)aliphatic moiety wherein C and/or H atoms can be substituted by O, Br, Cl, and Si atoms and which can comprise a bicyclic structural element;
F is a (cyclo)aliphatic moiety, wherein C and/or H atoms can be substituted by O, Br, Cl, and Si atoms;
a is 0, 1 or 2;
b is 1, 2 or 3;
m is 2, 3 or 4;
n is 1, 2, 3, 4, 5 or 6; and
Aryl is an aromatic moiety.

5. The dental composition of claim 1, wherein the carbosilane containing component is represented by the following formula (IIIb):

(IIIb)

wherein, independently selected from each other,
Aryl is an allyl-benzene;
A is a (cyclo)aliphatic moiety or aliphatic aromatic moiety;
B is an unsaturated moiety as terminal $C_2$ based olefinic moiety attached onto a spacer D;
D is a spacer having an aromatic aliphatic moiety with $C_7$ as α,3/4-toluenediyl with the phenyl ring attached to Si and the methylene group attached to aliphatic epoxy moiety B;
a is 0, 1 or 2;
b is 1, 2 or 3; and
n is 1.

6. The dental composition of claim 1, wherein the carbosilane containing component is represented by the following formula (IV):

(IV)

wherein, independently selected from each other,
A is an aliphatic or cycloaliphatic moiety ($C_1$ to $C_6$) or aromatic moiety ($C_6$ to $C_{14}$);
B is an unsaturated moiety attached onto a spacer D;
D is a spacer having a (cyclo)aliphatic moiety wherein C and/or H atoms can be substituted by O, Br, Cl, and Si atoms and which can comprise a bicyclic structural element;
G is (cyclo)aliphatic or aromatic or (cyclo)aliphatic aromatic or aromatic (cyclo)aliphatic moiety, wherein C and/or H atoms can be substituted by O, Br, Cl, and Si atoms;
a is 0, 1 or 2;
b is 1, 2 or 3;
m is 2, 3 or 4;
n is 1, 2, 3, 4, 5 or 6; and
Aryl is an aromatic moiety.

7. The dental composition of claim 1, wherein the carbosilane containing component is represented by the following formulas (IVa) or (IVb).

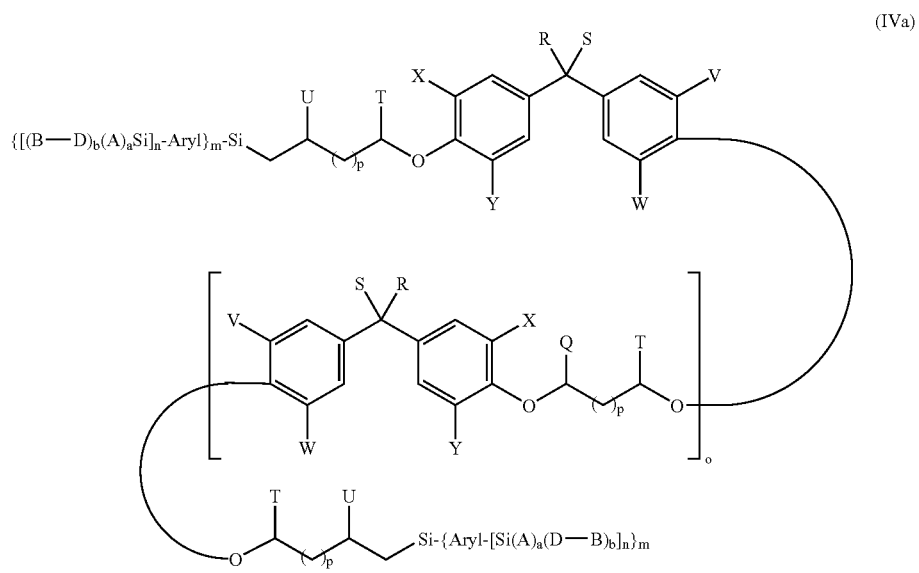
(IVa)

-continued

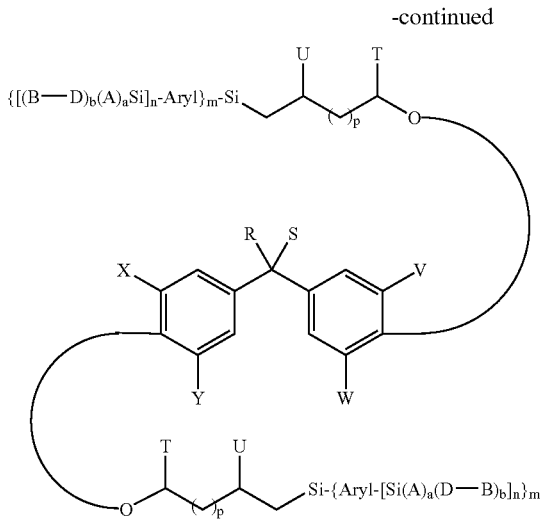
(IVb)

wherein, independently selected from each other,
A is an aliphatic or cycloaliphatic moiety ($C_1$ to $C_6$) or aromatic moiety ($C_6$ to $C_{14}$);
B is an unsaturated moiety attached onto a spacer D;
D is a spacer having a (cyclo)aliphatic moiety wherein C and/or H atoms can be substituted by O, Br, Cl, and Si atoms and which can comprise a bicyclic structural element;
a is 0, 1 or 2;
b is 1, 2 or 3;
p is 0, 1, 2, 3 or 4;
o is 0, 1, 2, 3, 4 or 5;
Q is H or $CH_3$;
each of R and S is H, $CH_3$, phenyl or alkadiyl;
each of T and U is H or $CH_3$;
each of V, W, X and Y is H, Br or Cl; and
Aryl is an aromatic moiety.

8. The dental composition of claim 1, wherein the Si—H functional component is an organopolysiloxane or carbosilane derived compound with Si-bonded hydrogen atoms.

9. The dental composition of claim 1, wherein the initiator comprises a light curing initiator or a redox curing initiator or a combination of both.

10. The dental composition of claim 1 further comprising a filler.

11. A container or cartridge filled with the dental composition of claim 1.

12. A kit of parts comprising a base part and a catalyst part, wherein the base part comprises the carbosilane containing component of claim 1, a Si—H functional component, and filler, and the catalyst part comprises initiator, and wherein an additive component is present either in the base part or the catalyst part or in the base part and the catalyst part.

13. A method of producing the dental composition of claim 1 comprising the steps of:
a) providing the carbosilane component of claim 1 and an initiator, and
b) mixing the components of step a),
wherein the carbosilane component is obtainable via a hydrosilylation reaction, a Grignard reaction, or an in situ Grignard reaction.

14. The method of claim 13, wherein the hydrosilylation reaction comprises reacting a Si—H functional carbosilane component and a diolefinic or acetylenic component.

15. The method of claim 13, wherein the Grignard reaction or in situ Grignard reaction comprises reacting a (poly)organometallic functional component or a (poly)halogenated precursor and a silicon containing component.

16. A dental material selected from a dental filling material, a crown or bridge material, a veneer material, an inlay and/or an onlay, wherein the dental material comprises the composition of claim 1.

17. A method for preparing a dental material comprising the steps of:
a) providing the dental composition of claim 1;
b) applying the dental composition to a surface;
c) curing the dental composition.

18. The dental composition of claim 10, wherein the filler comprises reinforcing and non-reinforcing fillers.

19. The dental composition of claim 18 further comprising an additive selected from modifiers, dyes, pigments, thixotropic agents, flow improvers, polymeric thickeners, surfactants, odorous substances, diluting agent(s) and flavourings.

20. The dental composition of claim 1, wherein the carbosilane containing component has a refractive index of at least 1.510.

21. The dental composition of claim 1, wherein the carbosilane containing component has a viscosity of at least 0.1 Pa*s.

22. The dental composition of claim 1, wherein the carbosilane containing component has a molecular mass of at least 250.

23. The dental composition of claim 1, wherein the opacity of the cured composition is at least 10%.

24. The dental composition of claim 1, wherein the compressive strength of the cured composition is at least 150 MPa.

25. The dental composition of claim 1, wherein the flexural strength of the cured composition is at least 50 MPa.

26. The dental composition of claim 19, wherein
the carbosilane containing component is present in an amount of at least 1% by weight,
the Si—H functional component is present in an amount of at least 1% by weight,
the initiator is present in an amount of at least 0.00005% by weight, calculated as elemental metal, the filler is present in an amount of at least 3% by weight, and
the additive is present in an amount of less than 25% by weight,
with respect to the cured composition.
27. A dental composition comprising:
an Si—H functional component;
an initiator; and
a carbosilane containing component selected from:
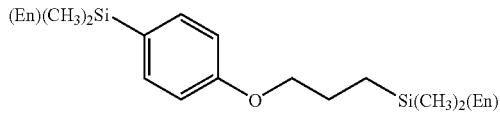
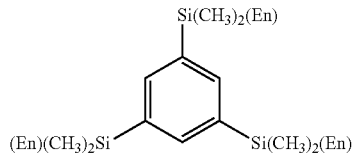
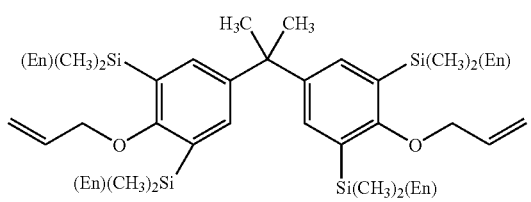
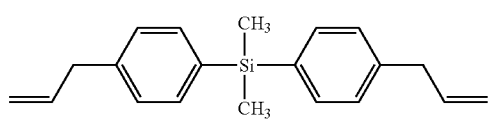
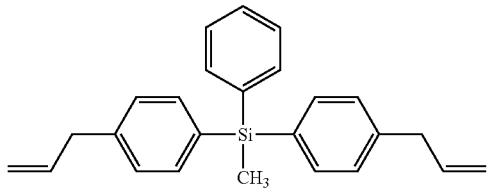
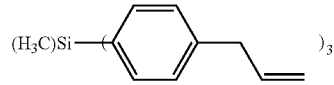
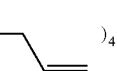
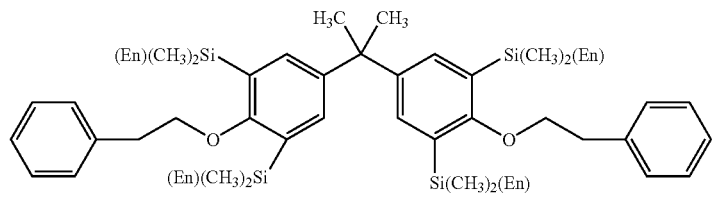
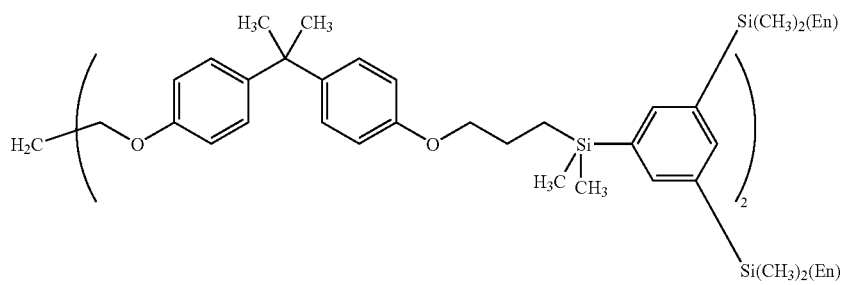
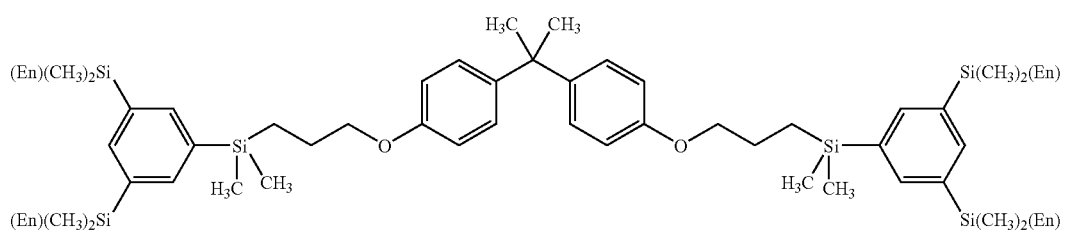

-continued

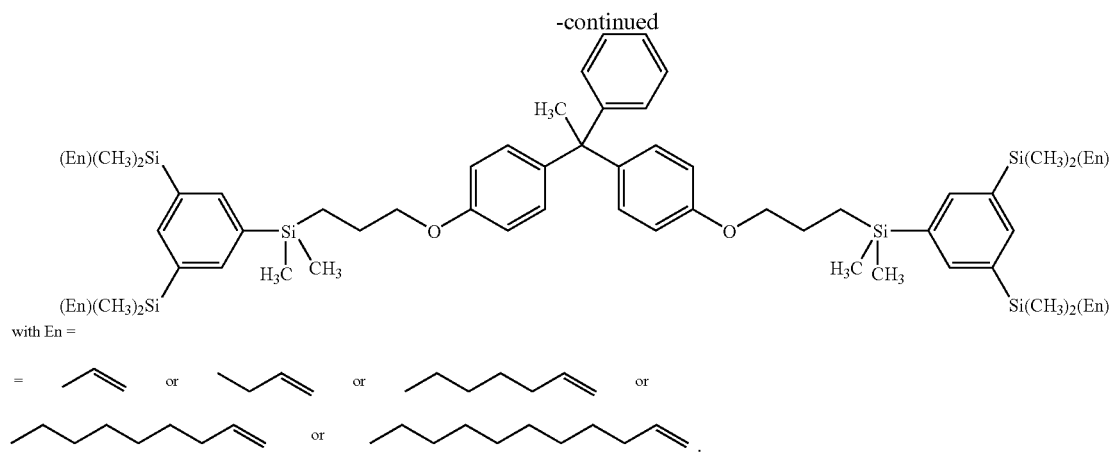

28. The dental composition of claim 27 wherein the compressive strength of the cured composition is at least 150 MPa.

29. The dental composition of claim 27 wherein the flexural strength of the cured composition is at least 50 MPa.

30. The dental composition of claim 27 wherein the Si—H functional component is an organopolysiloxane or carbosilane derived compound with Si-bonded hydrogen atoms.

31. A container or cartridge filled with the dental composition of claim 27.

32. A kit of parts comprising a base part and a catalyst part, wherein the base part comprises the carbosilane containing component of claim 27, a Si—H functional component and filler, and the catalyst part comprises initiator, and wherein an additive component is present either in the base part or the catalyst part or in the base part and the catalyst part.

33. A method of producing the dental composition of claim 27 comprising the steps of:
   a) providing the carbosilane component of claim 27 and an initiator, and
   b) mixing the components of step a), wherein the carbosilane component is obtainable via a hydrosilylation reaction, a Grignard reaction, or an in situ Grignard reaction.

34. The method of claim 33 wherein the hydrosilylation reaction comprises reacting a Si—H functional carbosilane component and a diolefinic or acetylenic component.

35. The method of claim 33 wherein the Grignard reaction or in situ Grignard reaction comprises retting a (poly)organometallic functional component or a (poly)halogenated precursor and a silicon containing component.

36. A dental material selected from a dental filling material, a crown or bridge material, a veneer material, an inlay and/or an onlay, wherein the dental material comprises the composition of claim 27.

37. A method for preparing a dental material comprising the steps of:
   a) providing the dental composition of claim 27;
   b) applying the dental composition to a surface;
   c) curing the dental composition.

* * * * *

UNITED STATES PATENT AND TRADEMARK OFFICE
CERTIFICATE OF CORRECTION

PATENT NO. : 7,662,869 B2  Page 1 of 1
APPLICATION NO. : 11/572071
DATED : February 16, 2010
INVENTOR(S) : Bissinger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 333 days.

Signed and Sealed this

Thirtieth Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,662,869 B2 | Page 1 of 5 |
| APPLICATION NO. | : 11/572071 | |
| DATED | : February 16, 2010 | |
| INVENTOR(S) | : Peter Bissinger | |

It is certified that error appears in the above-identified patent and that said Letters Patent is hereby corrected as shown below:

Title Page
After "Item [73] Assignee:", insert -- 3M ESPE AG, Seefeld, Germany --.

First Page, Column 2
Line 8-9, delete the word "flavorings" and insert -- flavourings --, therefor.

Page 2, Column 1
Line 1, delete the word "Hydosilylation," and insert -- Hydrosilylation, --, therefor.
Line 6, delete "Hydrosilylation,p107ff.," and insert -- Hydrosilylation, p107ff., --, therefor.

Column 1
Line 9, delete "Jul" and insert -- Jul. --, therefor.

Column 4
Line 46, delete "64(5),1066-1070." and insert -- 64(5), 1066-1070. --, therefor.

Column 6
Line 22, delete the word "know" and insert -- known --, therefor.

Signed and Sealed this
First Day of March, 2011

David J. Kappos
*Director of the United States Patent and Trademark Office*

CERTIFICATE OF CORRECTION (continued)
U.S. Pat. No. 7,662,869 B2

Column 2
Line 10-15, delete " 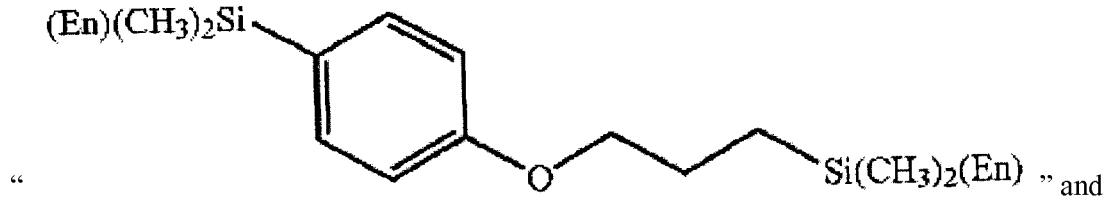 " and insert the same after " 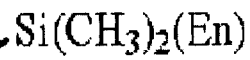 " on Col. 8, Line 24.

Line 46, delete "a=2 b=1," and insert -- a=2, b=1, --, therefor.
Line 57, delete "Si Aryl" and insert -- Si, Aryl --, therefor.

Column 2
Line 2, after "naphthyl" insert -- . --.

Column 11

Line 35-39, delete " 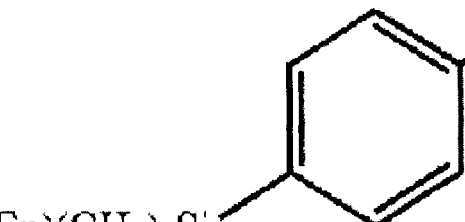 " and insert the same after " " on Col. 11, Line 49.

Column 2
Line 15, after "naphthyl" insert -- . --.

Column 18
Line 46, after "phenyl" insert -- . --.

Column 22
Line 59, delete "Ep" and insert -- En --, therefor.

Column 24
Line 56, after "phenyl" insert -- . --.

CERTIFICATE OF CORRECTION (continued)
U.S. Pat. No. 7,662,869 B2

Column 26
Line 20-25, delete

" 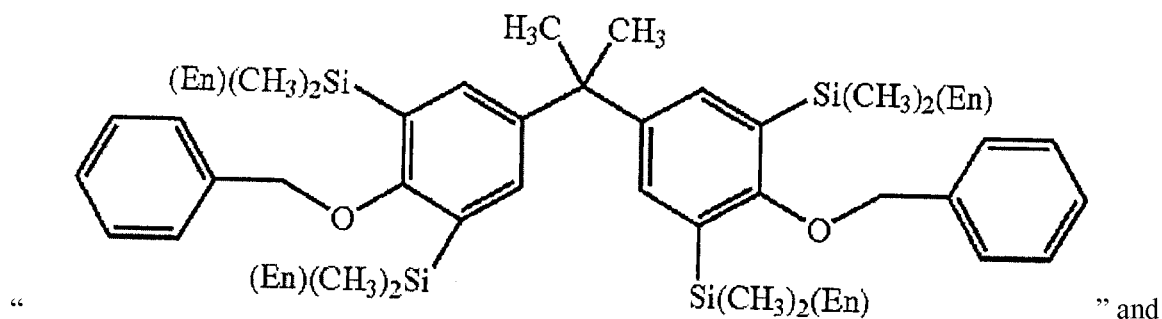 " and insert the same after " 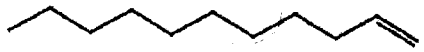 " on Col. 26, Line 36.

Column 3
Line 2, after "naphthyl" insert -- . --.

Column 28
Line 42, delete "(CH3)" and insert -- (CH$_3$) --, therefor.

Column 29-30
Line 8, delete

" 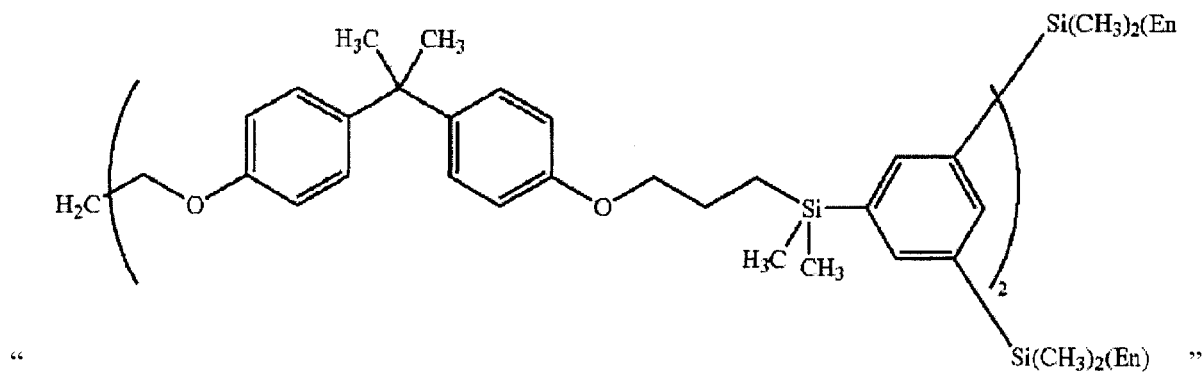 "

and insert the same after " 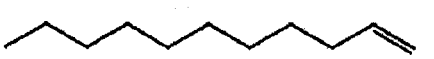 " on Col. 30, Line 12.

Column 3
Line 19, after "phenyl" insert -- . --.

CERTIFICATE OF CORRECTION (continued)

Column 31-32
Line 38, delete

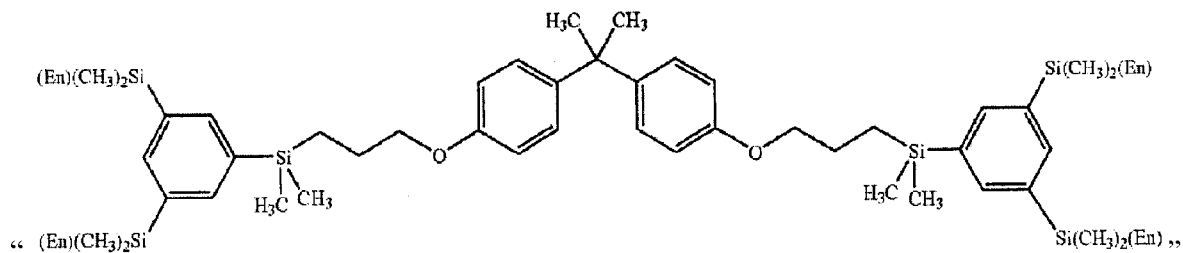

" (En)(CH₃)₂Si ", and insert the same after " 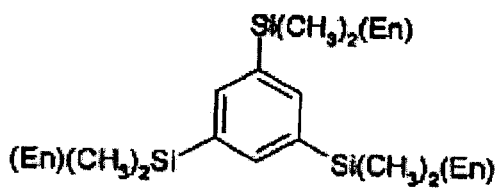 " on Col. 31, Line 42.

Column 52
Line 14, after "3,971,754)" insert -- . --.
Line 31, delete the word "moleculer" and insert -- molecular --, therefor.

Column 53
Line 28, delete the word "computes" and insert -- compules --, therefor.

Column 54
Line 36, in Claim 34, delete "atom:" and insert -- atom; --, therefor.
Line 39, in Claim 34, delete "atom," and insert -- atom; --, therefor.

Column 59

Line 6, in Claim 34, Before " 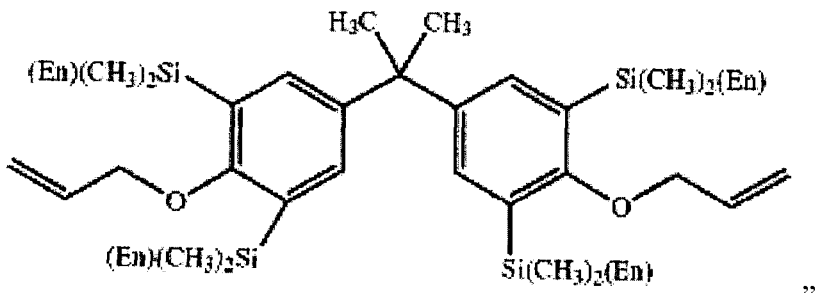 "

insert -- 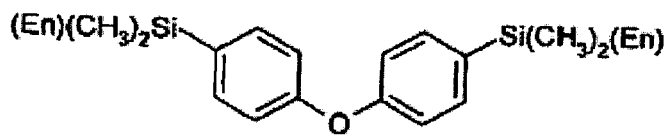 --.

CERTIFICATE OF CORRECTION (continued)
U.S. Pat. No. 7,662,869 B2

Column 61
Line 2, in Claim 34, delete "En=" and insert -- En= (D-B) --, therefor.
Line 34, in Claim 32, delete "component" and insert -- component, --, therefor.

Column 62
Line 29, in Claim 35, delete "retting" and insert -- reacting --, therefor.